United States Patent
Fishman et al.

(10) Patent No.: US 11,672,491 B2
(45) Date of Patent: Jun. 13, 2023

(54) VALIDATION OF THERAPEUTIC RADIATION TREATMENT

(71) Applicant: Sensus Healthcare, Inc., Boca Raton, FL (US)

(72) Inventors: Kalman Fishman, Boca Raton, FL (US); Brian P. Wilfley, Sunnyvale, CA (US); Christopher W. Ellenor, Toronto (CA); Donald Olgado, Palo Alto, CA (US); Chwen-Yuan Ku, San Jose, CA (US); Tobias Funk, Martinez, CA (US); Petre Vatahov, San Jose, CA (US); Christopher R. Mitchell, Pleasanton, CA (US); Yonatan Vainer, Giv'Atayim (IL)

(73) Assignee: EMPYREAN MEDICAL SYSTEMS, INC., Boca Raton, FL (US)

( * ) Notice: Subject to any disclaimer, the term of this patent is extended or adjusted under 35 U.S.C. 154(b) by 567 days.

(21) Appl. No.: 16/594,806

(22) Filed: Oct. 7, 2019

(65) Prior Publication Data
US 2020/0038691 A1 Feb. 6, 2020

Related U.S. Application Data

(63) Continuation-in-part of application No. 16/038,807, filed on Jul. 18, 2018, now Pat. No. 11,045,667, and (Continued)

(51) Int. Cl.
*A61B 6/02* (2006.01)
*A61N 5/10* (2006.01)
(Continued)

(52) U.S. Cl.
CPC .............. *A61B 6/025* (2013.01); *A61B 6/425* (2013.01); *A61B 6/4452* (2013.01); (Continued)

(58) Field of Classification Search
None
See application file for complete search history.

(56) References Cited

U.S. PATENT DOCUMENTS

| 4,401,406 A | 8/1983 | Rovira |
| 5,422,926 A | 6/1995 | Smith et al. |

(Continued)

FOREIGN PATENT DOCUMENTS

| CN | 204951972 U | 1/2016 |
| DE | 102010009276 A1 | 8/2011 |

(Continued)

OTHER PUBLICATIONS

International Search Report and Written Opinion dated Feb. 19, 2020 in PCT/US19/57191.
(Continued)

*Primary Examiner* — Angela M Hoffa
*Assistant Examiner* — Younhee Choi
(74) *Attorney, Agent, or Firm* — Fox Rothschild LLP

(57) ABSTRACT

Validation of a therapeutic radiation treatment involves using an applicator balloon surrounding an X-ray radiation source to support a plurality of X-ray sensor elements (XRSE). The XRSE are supported on the applicator balloon at distributed locations to sense applied radiation from the radiation source. At least one parameter of the applied radiation which has been sensed by the XRSE is compared to a corresponding parameter of a predetermined radiation treatment plan. Based on the comparing, a determination is made as to whether one or more requirements of the predetermined radiation treatment plan have been satisfied.

27 Claims, 20 Drawing Sheets

Related U.S. Application Data a continuation-in-part of application No. 15/941,547, filed on Mar. 30, 2018, now Pat. No. 10,607,802.

(60) Provisional application No. 62/820,452, filed on Mar. 19, 2019, provisional application No. 62/748,032, filed on Oct. 19, 2018.

(51) Int. Cl.
  *G01T 1/29* (2006.01)
  *A61B 6/00* (2006.01)
  *A61B 90/00* (2016.01)

(52) U.S. Cl.
  CPC .......... *A61B 6/4458* (2013.01); *A61B 6/5235* (2013.01); *A61B 90/39* (2016.02); *A61N 5/1067* (2013.01); *A61N 5/1071* (2013.01); *A61N 5/1083* (2013.01); *G01T 1/29* (2013.01); *A61B 2090/3966* (2016.02); *A61N 2005/1003* (2013.01)

(56) References Cited

U.S. PATENT DOCUMENTS

| | | | |
|---|---|---|---|
| 5,621,214 A | 4/1997 | Sofield | |
| 5,635,709 A | 6/1997 | Sliski et al. | |
| 5,635,721 A | 6/1997 | Bardi et al. | |
| 6,144,875 A | 11/2000 | Schweikard et al. | |
| 6,207,952 B1 | 3/2001 | Kan et al. | |
| 6,413,204 B1* | 7/2002 | Winkler | A61N 5/1015 600/3 |
| 6,826,254 B2 | 11/2004 | Mihara et al. | |
| 6,977,987 B2 | 12/2005 | Yamashita et al. | |
| 7,005,623 B2 | 2/2006 | Neuberger et al. | |
| 7,140,771 B2 | 11/2006 | Leek | |
| 7,186,022 B2 | 3/2007 | Charles, Jr. et al. | |
| 7,188,999 B2 | 3/2007 | Mihara et al. | |
| 7,193,220 B1 | 3/2007 | Navarro | |
| 7,200,203 B2 | 4/2007 | Cocks et al. | |
| 7,201,715 B2* | 4/2007 | Burdette | A61B 8/5238 600/7 |
| 7,239,684 B2 | 7/2007 | Hara et al. | |
| 7,263,170 B2 | 8/2007 | Pellegrino | |
| 7,266,176 B2 | 9/2007 | Allison et al. | |
| 7,283,610 B2 | 10/2007 | Low et al. | |
| 7,356,120 B2 | 4/2008 | Main et al. | |
| 7,420,160 B2 | 9/2008 | Delaperriere et al. | |
| 7,505,559 B2 | 3/2009 | Kuduvalli | |
| 7,590,219 B2 | 9/2009 | Maurer, Jr. et al. | |
| 7,605,365 B2 | 10/2009 | Chen et al. | |
| 7,619,374 B2 | 11/2009 | Aoi et al. | |
| 7,656,998 B2 | 2/2010 | Main et al. | |
| 7,686,755 B2 | 3/2010 | Smith et al. | |
| 7,693,257 B2 | 4/2010 | Allison | |
| 7,713,205 B2 | 5/2010 | Fu et al. | |
| 7,894,649 B2 | 2/2011 | Fu et al. | |
| 7,902,515 B2 | 3/2011 | Navarro | |
| 8,050,384 B2 | 11/2011 | Carol et al. | |
| 8,126,114 B2 | 2/2012 | Naylor et al. | |
| 8,139,714 B1 | 3/2012 | Sahadevan | |
| 8,180,020 B2 | 5/2012 | Kilby et al. | |
| 8,183,522 B2 | 5/2012 | Celi de la Torre et al. | |
| 8,295,435 B2 | 10/2012 | Wang et al. | |
| 8,303,476 B2 | 11/2012 | Francescatti et al. | |
| 8,321,179 B2 | 11/2012 | Simon et al. | |
| 8,332,072 B1 | 12/2012 | Schaible et al. | |
| 8,520,801 B2 | 8/2013 | Henning | |
| 8,559,596 B2 | 10/2013 | Thomson et al. | |
| 8,559,598 B2 | 10/2013 | Kindlein et al. | |
| 8,602,647 B2 | 12/2013 | Navarro | |
| 8,655,429 B2 | 2/2014 | Kuduvalli et al. | |
| 8,660,235 B2 | 2/2014 | Koehler | |
| 8,792,613 B2 | 7/2014 | Gardner et al. | |
| 8,804,901 B2 | 8/2014 | Maurer, Jr. et al. | |
| 8,917,813 B2 | 12/2014 | Maurer, Jr. | |
| 8,929,511 B2 | 1/2015 | van der Veen et al. | |
| 8,934,605 B2 | 1/2015 | Maurer, Jr. et al. | |
| 8,989,846 B2 | 3/2015 | Kuduvalli et al. | |
| 8,995,616 B2 | 3/2015 | van der Veen et al. | |
| 9,036,787 B2 | 5/2015 | de Jager | |
| 9,040,945 B1 | 5/2015 | Hayman | |
| 9,076,201 B1 | 7/2015 | Negahdar et al. | |
| 9,108,048 B2 | 8/2015 | Maurer, Jr. et al. | |
| 9,168,391 B2 | 10/2015 | Henning et al. | |
| 9,289,268 B2 | 3/2016 | Ramraj et al. | |
| 9,333,031 B2 | 5/2016 | Salahieh et al. | |
| 9,415,239 B2 | 8/2016 | Lubock et al. | |
| 9,561,009 B2 | 2/2017 | Woudstra et al. | |
| 9,616,251 B2 | 4/2017 | Filiberti et al. | |
| 9,724,066 B2 | 8/2017 | Van Der Veen et al. | |
| 9,743,912 B2 | 8/2017 | Fichtinger et al. | |
| 10,327,716 B2 | 6/2019 | Mazin | |
| 10,350,437 B2 | 7/2019 | Fishman | |
| 10,398,519 B2 | 9/2019 | Kim et al. | |
| 10,607,802 B2 | 3/2020 | Fishman et al. | |
| 10,646,726 B2 | 5/2020 | Fishman | |
| 2001/0049475 A1 | 12/2001 | Bucholz et al. | |
| 2002/0077545 A1 | 6/2002 | Takahashi et al. | |
| 2002/0085668 A1 | 7/2002 | Blumhofer et al. | |
| 2002/0136439 A1 | 9/2002 | Ruchala et al. | |
| 2004/0218721 A1 | 11/2004 | Chornenky et al. | |
| 2004/0227056 A1 | 11/2004 | Neuberger et al. | |
| 2005/0101824 A1 | 5/2005 | Stubbs | |
| 2005/0111621 A1 | 5/2005 | Riker et al. | |
| 2005/0276377 A1 | 12/2005 | Carol | |
| 2006/0020195 A1 | 1/2006 | Falco et al. | |
| 2006/0085053 A1 | 4/2006 | Anderson et al. | |
| 2007/0076851 A1 | 4/2007 | Pellegrino | |
| 2008/0009659 A1 | 1/2008 | Smith et al. | |
| 2008/0170663 A1 | 7/2008 | Urano et al. | |
| 2008/0198970 A1 | 8/2008 | Kirshner et al. | |
| 2009/0161826 A1 | 6/2009 | Gertner et al. | |
| 2009/0209805 A1 | 8/2009 | Lubock | |
| 2009/0250618 A1* | 10/2009 | Simon | A61N 5/1071 250/371 |
| 2010/0030463 A1 | 2/2010 | Tomizawa | |
| 2010/0040198 A1 | 2/2010 | Comer et al. | |
| 2010/0237259 A1 | 9/2010 | Wang | |
| 2010/0274151 A1 | 10/2010 | Chi et al. | |
| 2011/0105822 A1 | 5/2011 | Roeder | |
| 2011/0257459 A1 | 10/2011 | Sutton | |
| 2012/0016175 A1 | 1/2012 | Roberts et al. | |
| 2012/0037807 A1 | 2/2012 | Ujhazy et al. | |
| 2012/0259197 A1 | 10/2012 | Isham | |
| 2012/0294414 A1 | 11/2012 | Koehler | |
| 2013/0025055 A1 | 1/2013 | Saracen et al. | |
| 2013/0116555 A1 | 5/2013 | Kuzelka | |
| 2013/0131428 A1 | 5/2013 | Jiang et al. | |
| 2013/0217947 A1 | 8/2013 | Fishman | |
| 2013/0231516 A1 | 9/2013 | Loo et al. | |
| 2013/0345718 A1 | 12/2013 | Crawford et al. | |
| 2014/0029727 A1 | 1/2014 | Ono | |
| 2014/0054465 A1 | 2/2014 | Berke | |
| 2014/0086388 A1 | 3/2014 | Yamada et al. | |
| 2014/0105361 A1 | 4/2014 | Vogtmeier et al. | |
| 2014/0121501 A1 | 5/2014 | Fichtinger et al. | |
| 2014/0171919 A1 | 6/2014 | Blacker | |
| 2014/0185778 A1 | 7/2014 | Lee et al. | |
| 2014/0205067 A1 | 7/2014 | Carol et al. | |
| 2014/0257013 A1* | 9/2014 | D'Andrea | A61N 5/1071 600/2 |
| 2014/0348288 A1 | 11/2014 | Boyd et al. | |
| 2015/0265306 A1 | 9/2015 | Andrews | |
| 2015/0265353 A1 | 9/2015 | Andrews | |
| 2015/0265366 A1 | 9/2015 | Andrews | |
| 2015/0366546 A1 | 12/2015 | Kamen et al. | |
| 2016/0106387 A1 | 4/2016 | Kahn et al. | |
| 2016/0184032 A1 | 6/2016 | Romo et al. | |
| 2016/0193482 A1 | 7/2016 | Fahrig et al. | |
| 2017/0001939 A1 | 1/2017 | Sookraj et al. | |
| 2017/0004267 A1 | 1/2017 | Svatos et al. | |
| 2017/0296289 A1 | 10/2017 | Andrews et al. | |
| 2017/0368369 A1 | 12/2017 | Heinrich et al. | |
| 2018/0015303 A1 | 1/2018 | Fishman | |

(56) References Cited

U.S. PATENT DOCUMENTS

| | | |
|---|---|---|
| 2018/0286623 A1 | 10/2018 | Fishman et al. |
| 2019/0022418 A1 | 1/2019 | Fishman |
| 2019/0060674 A1 | 2/2019 | Fishman |
| 2019/0103869 A1 | 4/2019 | Hannibal |
| 2020/0038691 A1 | 2/2020 | Fishman et al. |
| 2020/0101325 A1 | 4/2020 | Ollila et al. |
| 2020/0121957 A1 | 4/2020 | Fishman et al. |

FOREIGN PATENT DOCUMENTS

| | | |
|---|---|---|
| JP | S50-011690 A | 2/1975 |
| JP | S54111296 A | 8/1979 |
| JP | S60-110121 A | 6/1985 |
| JP | H06-500661 A | 1/1994 |
| JP | 2011-518627 A | 6/2011 |
| JP | 2014-520363 A | 8/2014 |
| JP | 2017-027873 A | 2/2017 |
| RU | 2013147424 A | 4/2015 |
| RU | 2557466 C2 | 7/2015 |
| WO | 9204727 A1 | 3/1992 |
| WO | 2010030463 | 3/2010 |
| WO | 2010065740 A2 | 6/2010 |
| WO | 2017044441 A1 | 3/2017 |

OTHER PUBLICATIONS

Extended European Search Report dated Jan. 31, 2020 in EP 17828486.5 filed Jan. 23, 2019.
Extended European Search Report dated Jul. 9, 2020 in EP 18776334.
International Search Report in PCT/US18/25438 dated Aug. 8, 2018.
International Search Report dated Sep. 21, 2017 in PCT/US17/041986.
International Search Report dated Oct. 29, 2018 in PCT/US18/46663.
International Search Report mailed in PCT/IB2018/055352 dated Nov. 26, 2018.

* cited by examiner

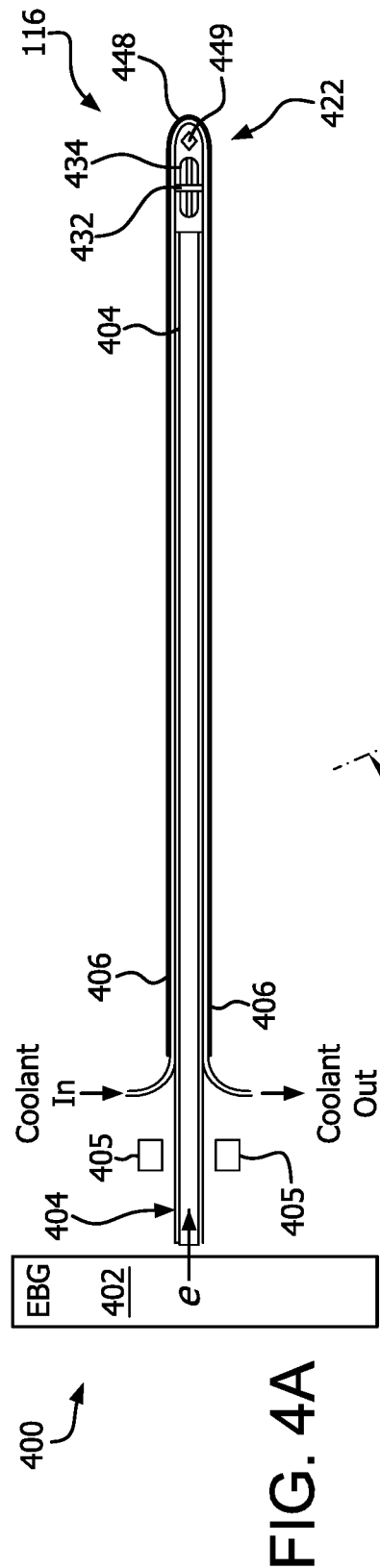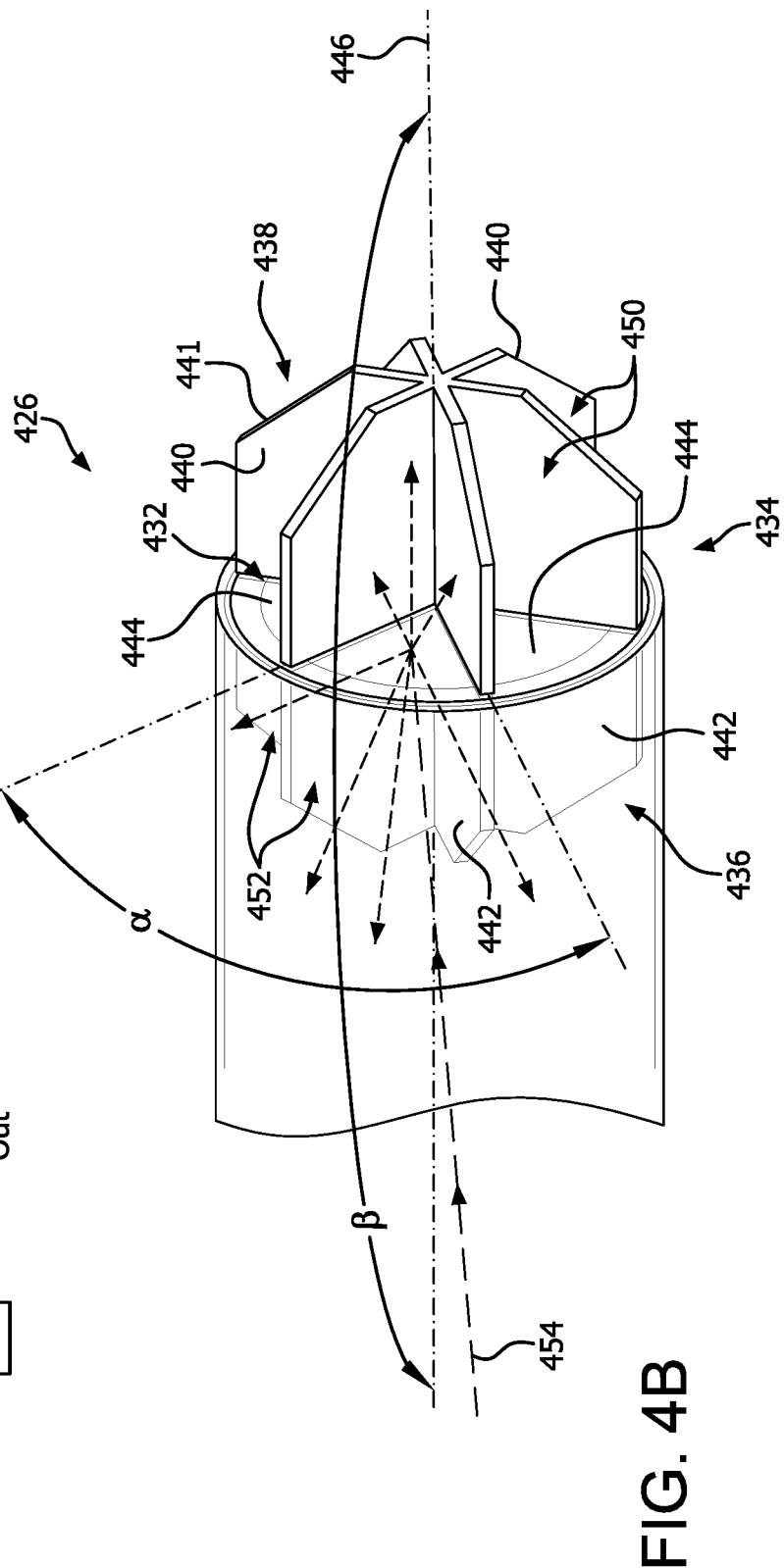

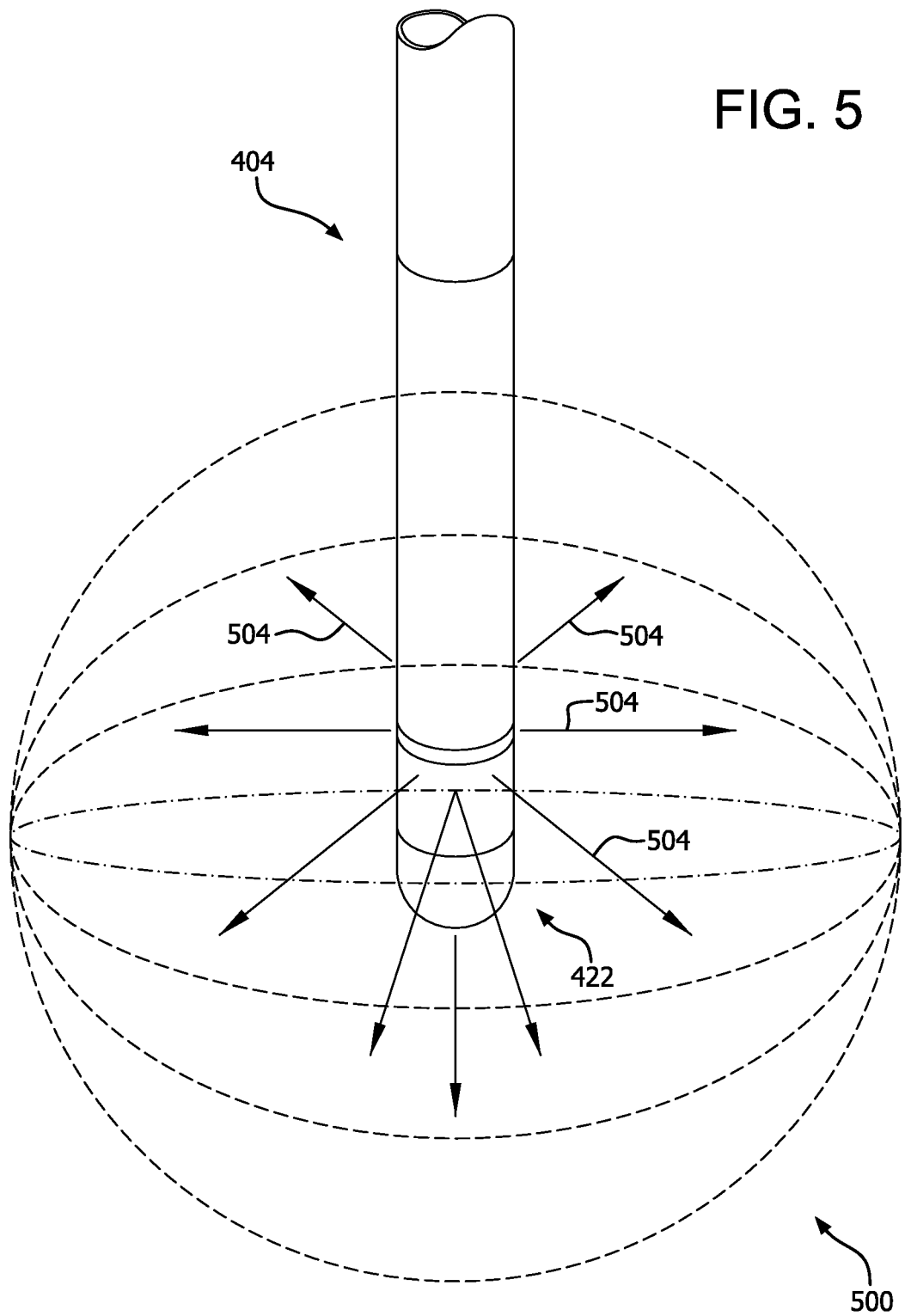

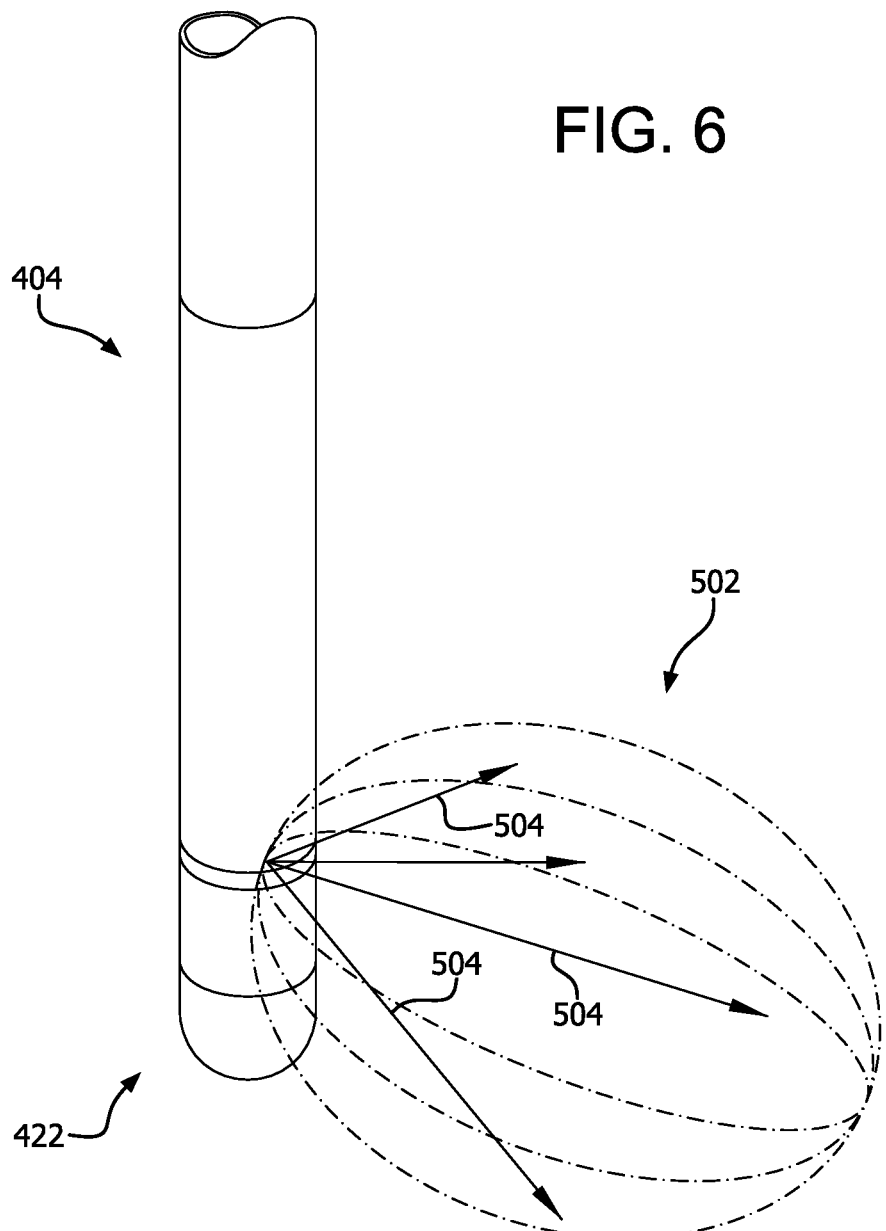

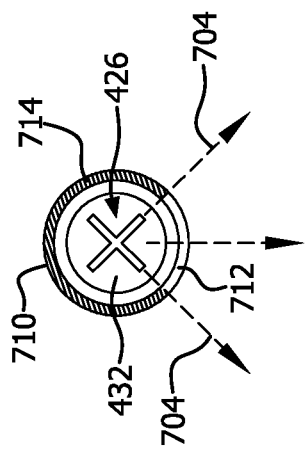
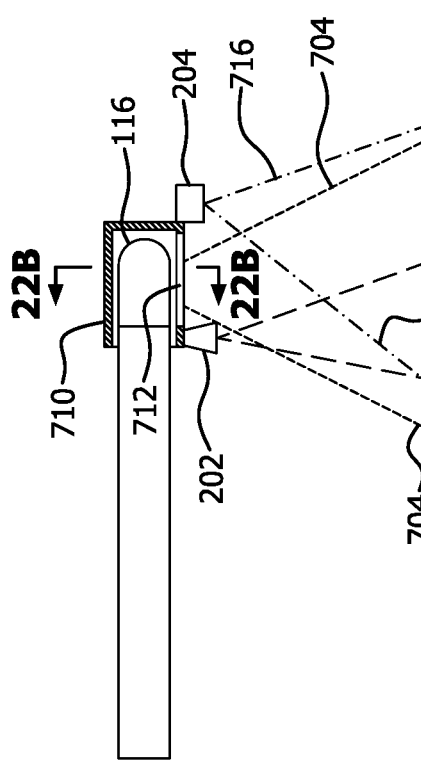
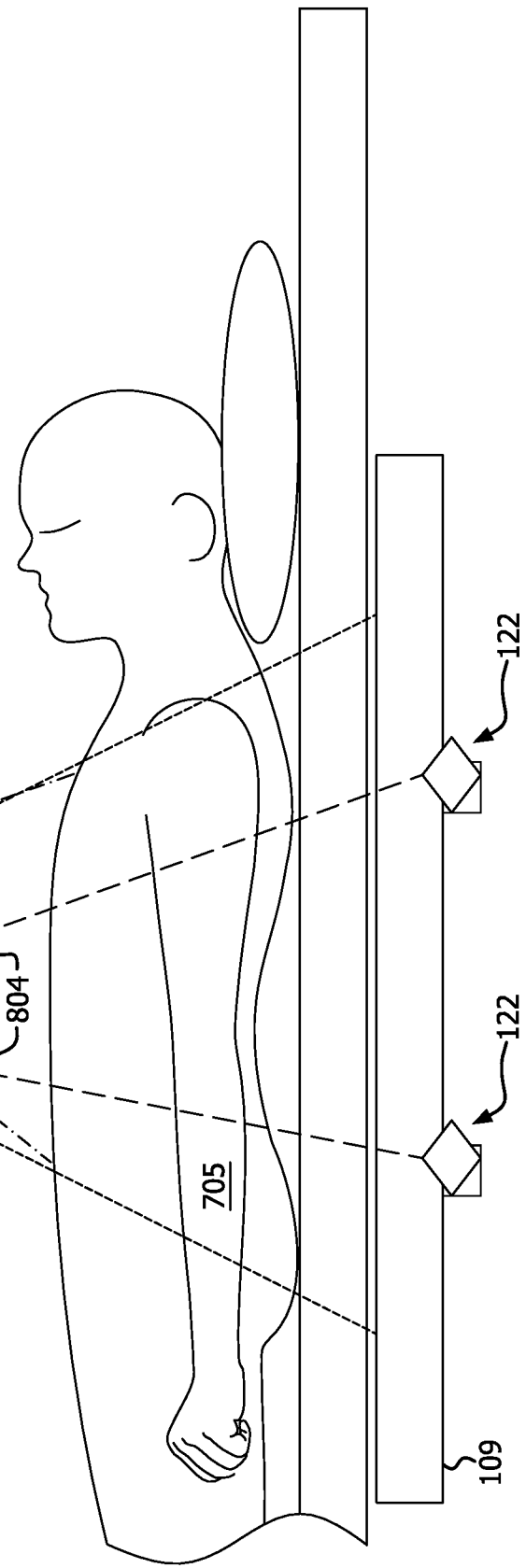

VALIDATION OF THERAPEUTIC RADIATION TREATMENT

CROSS-REFERENCE TO RELATED APPLICATIONS

This application is a continuation-in-part of U.S. patent application Ser. No. 16/038,807 filed Jul. 18, 2018, and is also a continuation-in-part of U.S. patent application Ser. No. 15/941,547 filed Mar. 30, 2018. This application further claims the benefit of U.S. Provisional Application No. 62/748,032 filed on Oct. 19, 2018, and also claims the benefit of U.S. Provisional Application No. 62/820,452 filed on Mar. 19, 2019.

BACKGROUND

Statement of the Technical Field

The technical field of this disclosure concerns medical equipment, and more particularly concerns X-ray systems and methods for use in medical facilities.

Description of the Related Art

Ionizing radiation is commonly used for different purposes in the medical field. One such purpose involves therapeutic treatment of patients. For example, radiation is often used to damage cancer cells so that they will no longer grow and spread within a patient. One example of a particular type of radiation therapy is intraoperative radiation therapy (IORT). As is known, IORT is a radiation treatment that is administered to a tumor bed during surgery. This treatment is intended to damage any cancer cells which may remain in the tumor bed after the tumor has been removed. Another type of radiation therapy is Brachytherapy, which is used to treat cancer by positioning a radiation source inside the body of a cancer patient.

SUMMARY

This document concerns a method for validation of a therapeutic radiation treatment. An applicator balloon surrounds a radiation source which produces X-rays. The balloon is used to control a distance between the radiation source and patient tissue comprising a radiation treatment site. A plurality of X-ray sensor elements (XRSE) are supported on the applicator balloon at a plurality of distributed locations to sense applied radiation from the radiation source. The method further involves comparing at least one parameter of the applied radiation which has been sensed by the XRSE to a corresponding parameter of a predetermined radiation treatment plan. Based on the comparing, a determination is made as to whether one or more requirements of the predetermined radiation treatment plan have been satisfied.

In some scenarios, the at least one parameter of the applied radiation can be selected from the group consisting of a duration of the applied radiation, an intensity of the applied radiation, and a three-dimensional radiation pattern associated with the applied radiation. According to one aspect, the comparing involves comparing a plurality of sensed radiation intensity values detected in each of a plurality of different beam vector directions extending from the radiation source, to a plurality of corresponding expected radiation intensity values for the plurality of different beam vector directions as specified by a planned three-dimensional radiation pattern. The planned three-dimensional radiation pattern is specified by the predetermined radiation treatment plan. The method can further involve using measurement data generated by the XRSE to generate estimated information about a three-dimensional radiation pattern produced by the radiation source for portions of the three-dimensional radiation pattern that are not directly sensed by the XRSE. The estimated information is used to facilitate the comparing with regard to one or more of the beam vector directions for which actual measurement data from the plurality of XRSE is not available.

In some scenarios, the method can also dynamically controlling the radiation source during a treatment session responsive to measurement data from the XRSE. In such scenarios, the dynamic control of the radiation source involves selectively conforming a three-dimensional radiation pattern produced by the radiation source to a planned three-dimensional radiation pattern specified by the predetermined radiation treatment plan. The method can also involve dynamically controlling the radiation source during a treatment session responsive to measurement data from the XRSE to selectively control a radiation dosage applied to the patient tissue. In this regard, the radiation source can be controlled to conform an applied radiation dosage at a plurality of patient tissue locations to a planned radiation dosage specified by the predetermined radiation treatment plan for the plurality of patient tissue locations.

The plurality of patient tissue locations may be aligned with a plurality of different beam vector directions originating from the radiation source. Accordingly, the applied radiation dosage at each of the plurality of patient tissue locations can be selectively controlled during the treatment session by dynamically varying a three-dimensional radiation pattern produced by the radiation source during the treatment session. In other scenarios, the applied radiation dosage at each of the plurality of patient tissue locations can be dynamically controlled during the treatment session by selectively varying a duration of time that radiation is applied at each of the plurality of patient tissue locations.

In the method described herein the radiation source can also be used to facilitate production of a plurality of two-dimensional (2D) X-ray projection images of the patient tissue. Thereafter, the plurality of 2D X-ray projection images can be used to facilitate a digital tomosynthesis ("DT") operation. The results of the DT operation are then used to facilitate development of the predetermined radiation treatment plan. The production of the 2D X-ray projection images and the DT operation can be performed before, during or after a surgical procedure to facilitate intra-operative radiation therapy. The results of the DT operation can be used in a deformable image fusing operation. In this way, a pre-operative volumetric imaging of the subject patient is deformably fused with a plurality of image sections or slices obtained from the DT operation.

The production of the plurality of the 2D X-ray projection images as described herein can involve using a robotic arm to precisely control a position of the radiation source relative to the patient tissue. An X-ray imaging array is then used to selectively capture the plurality of the 2D X-ray projection images as the radiation source is moved by the robotic arm to a plurality of different locations over a predetermined path. Concurrent with obtaining each 2D projection image, a location of the radiation source is determined relative to the X-ray imaging array. The predetermined path of the radiation source can be controlled so as to define an arc which has a central angle of between 15° and 40° to facilitate the DT operations. After the DT operations are complete, the robotic arm is used to reposition the radiation source with respect to the patient tissue so that the radiation source is disposed at a treatment location. In some scenarios, this treatment location can be internal to the patient to facilitate intra-operative radiation therapy. Once positioned at the treatment location, the radiation source while is used to carry out a therapeutic X-ray treatment of the patient tissue. Accordingly, the radiation source can be selectively controlled so as to produce a first X-ray beam pattern for purposes of obtaining the 2D projection images, and a second X-ray beam pattern for purposes of a therapeutic treatment specified by the radiation treatment plan.

BRIEF DESCRIPTION OF THE DRAWINGS

This disclosure is facilitated by reference to the following drawing figures, in which like numerals represent like items throughout the figures, and in which:

FIG. 4A is a schematic diagram that is useful for understanding an controlled beam X-ray source that can be used with the robotic X-ray system.

FIG. 4B is a drawing which is useful for understanding how a X-ray beam can be sculpted or shaped to form a specific beam pattern using het X-ray system in FIG. 4B.

FIG. 5 is an example of a first beam pattern that can be created using the controlled beam X-ray source.

FIG. 6 is an example of a second beam pattern that can be created using the controlled beam X-ray source.

FIGS. 22A and 22B are a series of drawings that are useful for understanding certain X-ray system components that facilitate Digital Tomosynthesis operations.

DETAILED DESCRIPTION

Figure 1:
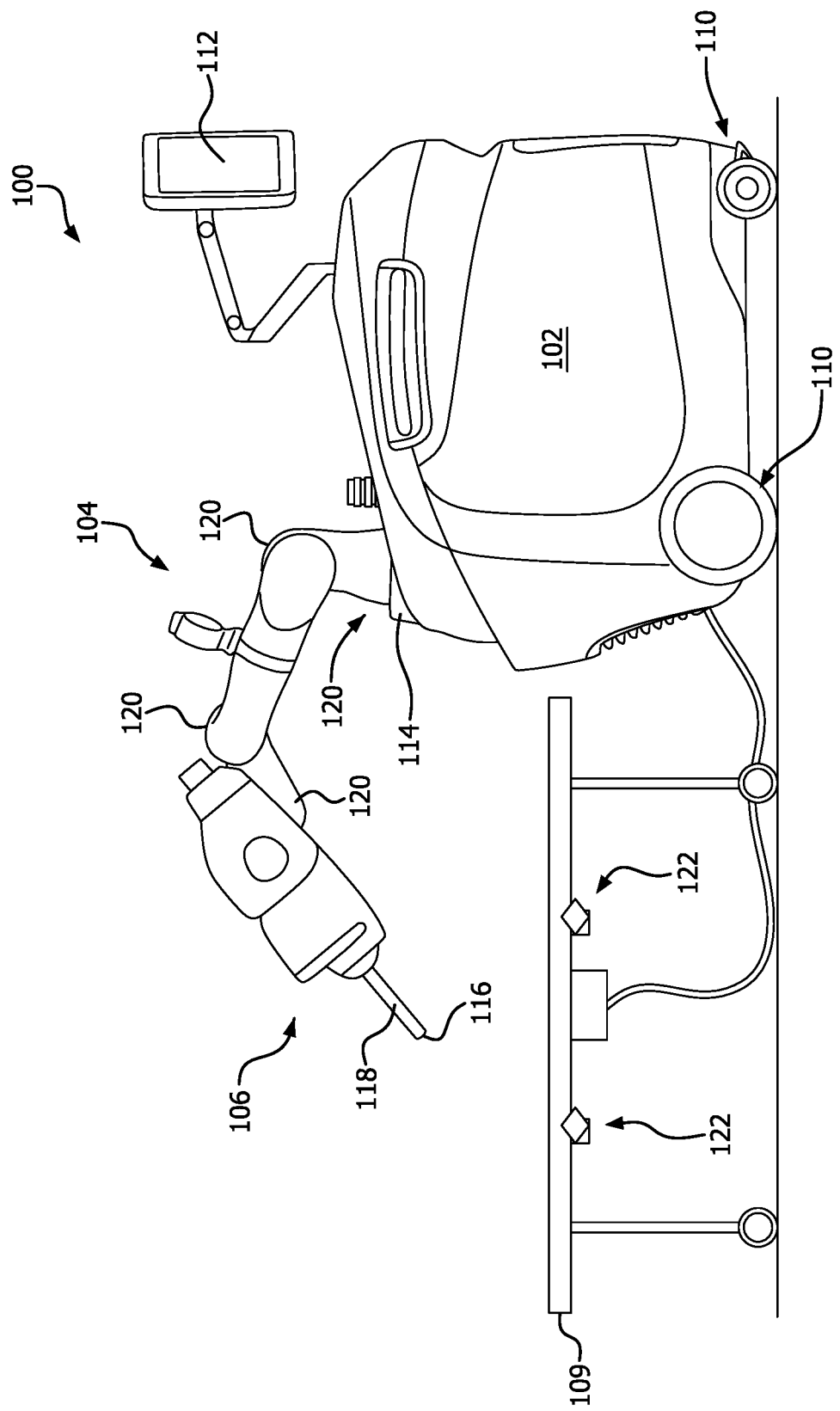
FIG. 1 is a diagram which is useful for understanding an implementation of a robotic X-ray system.

It will be readily understood that the solution described herein and illustrated in the appended figures could involve a wide variety of different configurations. Thus, the following more detailed description, as represented in the figures, is not intended to limit the scope of the present disclosure, but is merely representative of certain implementations in various different scenarios. While the various aspects are presented in the drawings, the drawings are not necessarily drawn to scale unless specifically indicated.

A robotic X-ray system disclosed herein comprises an X-ray generating system, and includes an X-ray treatment head which is secured to a movable end portion of a robotic arm. X-ray energy is emanated or radiated from the treatment head when the X-ray generating system is activated. In some scenarios, the X-ray treatment head can be disposed at the tip end of an elongated applicator body which is secured to the robotic arm by a base portion. By controlling the position of one or more robotic arm joints, the robotic arm can control a position of the treatment head relative to the patient. The highly adaptive nature of the robotic arm and the X-ray source in such an X-ray system can permit the same system to carry out therapeutic X-ray treatments, including but not limited to Brachytherapy and IORT.

System Overview

Robotic Sculpted Beam X-ray System 100 as shown in FIG. 1 can comprise a portable base unit or cart 102 (e.g. a movable cart on casters) to which a robotic arm 104 is attached. A head unit 106 is fixed to a first end of the robotic arm distal from a second end of the robotic arm which is attached to the portable base unit. The head unit 106 is comprised of an X-ray source which is part of an X-ray system for generating X-ray radiation. A power supply and control unit for the X-ray system (including the robotic arm) can be integrated within the base unit 102.

The base unit 102 is advantageously a compact unit such as one with a 30"×48" footprint and can be mounted on casters 110 for ease of maneuverability. The base unit 102 can include a power lead (not shown) for optionally providing power to all of the components housed in or connected to the base unit 102. In this regard, the base unit 102 can contain one or more components of an X-ray system as described in further detail herein with respect to FIG. 2. For example, a display device 112 is shown mounted to the base unit 102 to facilitate a user interface. Likewise, a user interface device such as a keyboard, mouse or touchpad, can be included in the base unit. In some scenarios, the display device 112 can be associated with a computer workstation (not shown in FIG. 1).

A rigid mechanical mount 114 is provided on the base unit 102 for mounting the robotic arm 104 in a fixed location on the base unit. In a solution presented herein, the robotic arm can be used to control a position of the head unit 106 with great precision. Control of the position of head unit 106 also facilitates control over the position of a treatment head 116 from which X-ray energy is emitted during an X-ray session. This controlled position can be a static position in which the treatment head 116 does not move during a time when X-ray radiation is being applied. However, the robotic arm 104 can also facilitate a predetermined motion or movement of the treatment head during an X-ray session. In some scenarios, the movement can occur concurrent with the application of the X-ray radiation. In other scenarios, the application of X-ray radiation can be temporarily interrupted while the robotic arm repositions the treatment head.

In some scenarios, an elongated X-ray applicator body 118 extends from a portion of the head unit 106 to the treatment head 116. The robotic arm 104 is articulated with appropriate robotic joints or articulation members 120 under the control of the control unit. Although not shown in FIG. 1, more or fewer articulation members 120 can be provided at different points of robotic arm 104. Such articulation members 120 can increase or decrease a number of degrees of freedom for placing, orienting and moving the X-ray treatment head 116. Moreover, the number of articulation members illustrated in FIG. 1 is solely for ease of illustration. The present disclosure contemplates that the any number of articulation points can be provided so as to provide any number of degrees of freedom in robotic arm 104 as may be required for dynamically positioning and orienting the X-ray treatment head 116 with respect to the patient.

In some scenarios, the robotic arm 104 is a robotic system that provides freedom of movement about multiple orthogonal axes (e.g. up to seven axes) and includes lightweight force and torque sensors to ensure safe operation with humans without the need for a safety fence. Exemplary robots of this kind are commercially available from various sources. For example, KUKA Roboter GmbH of Augsburg Germany (KUKA) manufactures a line of direct human-robot collaboration (HRC) capable lightweight robots which are suitable for direct human-robot interaction. These robots include the LBR iiwa model and/or the LBR iisy model produced by KUKA. Robots of this kind are well suited for the delicate operations described herein because they include high-grade joint torque sensors included in all six axes, which can detect the slightest of external forces resulting from contact with objects, and can respond by immediately reducing a level of force and speed associated with robot movements. The robotic arm 104 will precisely maintain a position of the X-ray treatment head relative to a subject patient. In order to accomplish this result, the robotic arm can move along multiple motion axes (e.g., up to seven motion axes) to maintain a relative position of the X-ray treatment head at a particular location and/or along a predetermined movement path.

The X-ray generating system in some scenarios can be distributed between the base unit 102 and the head unit 106. A power and/or control signal conduit (not shown in FIG. 1) can facilitate communication of power and/or control signals between the base unit 102 and the head unit 106. These signals can be used to control and facilitate operation of the X-ray generating system. In some scenarios, high voltage cables, fluid conduits, and control circuitry may not be included as part of the robotic arm, but can instead comprise a separate control cable bundle which simply attaches to the X-ray treatment head.

Figure 2:
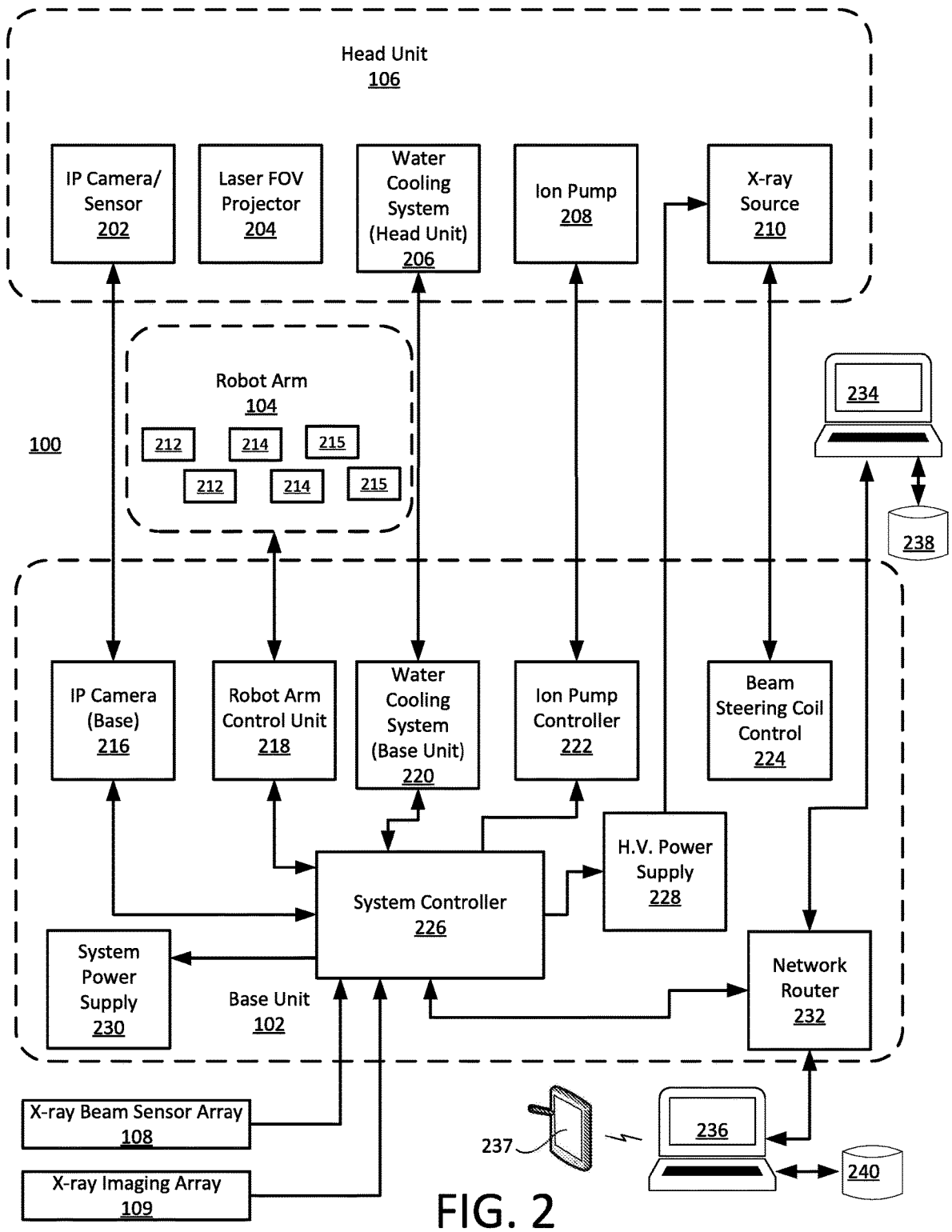
FIG. 2 is a block diagram that is useful for understanding an architecture of a robotic X-ray system.

Referring now to FIG. 2 there is shown a high level block diagram representation of Robotic Sculpted Beam X-ray System 100 which is useful for understanding certain aspects of a solution presented herein. The block diagram shows the main subsystems including the base unit 102, the robot arm 104, and the head unit 106 as described in relation to FIG. 1, and includes details of certain components that can be distributed among these various subsystems. For example, the base unit can be comprised of a system power supply 230, an internet protocol (IP) camera base component 216, and a robot arm control unit 218. The base unit 102 can also include various base unit components associated with an X-ray generating system. For example, these components can include a high voltage power supply 228, an ion pump controller 222, a beam steering coil control 224, and a water cooling system base unit portion 220. In some scenarios, the water cooling system can use water as a coolant to carry heat away from certain components of the X-ray generating system described herein. Although referred to herein as a water cooling system, it should be understood that water is just one example of a suitable coolant which can be used for this purpose. As will be understood by those skilled in the art, other types of fluid coolants can also be used for this purpose.

A system controller 226 is provided to control the overall operation of the Robotic Sculpted Beam X-ray System 100. As such, the system controller 226 can be communicatively connected to one or more of the IP camera base component 216, robot arm control unit 218, water cooling system base unit portion 220, the ion pump controller 222, system power supply 230, and the high voltage power supply 228.

The head unit 106 can include various head unit components associated with the X-ray generating system including a water cooling system head unit portion 206, and an ion pump 208. As explained below in further detail, the ion pump can comprise a part of an Electron Beam Generator (EBG) for an X-ray source 210. The X-ray source 210 can include electron beam steering coils (not shown in FIG. 2) which are used to help shape an X-ray beam. The ion pump 208 operates under the control of the ion pump controller 222, and the X-ray source 210 operates under the control of the beam steering coil control unit 224. In some scenarios, the X-ray source 210 can be configured so that X-ray radiation is emitted from the treatment head 116 disposed on the movable end of the robotic arm 104. The X-ray generating system described herein can be configured to facilitate treatment of a patient in accordance with various treatment methods (e.g. IORT and/or Brachytherapy methods) which are now known or known in the future.

The water cooling system head unit portion 206 can operate cooperatively with, and under the control of, the water cooling system base unit portion 220. For example, the water cooling system head unit portion 206 can be configured to facilitate a flow of cooling water (or any other suitable coolant) to one or more of the components associated with the X-ray generating system. The head unit 106 can also include an IP camera/sensor head unit component 202, a laser field of view (FOV) projector component 204. The IP camera/sensor head unit is configured to capture one or more images which are useful for facilitating an X-ray imaging and/or treatment session. The purpose and function of the IP camera/sensor system (202, 216) will be described in greater detail below.

Communication of data, fluids and/or control signals between the various components of Robotic Sculpted Beam X-ray System 100 that are disposed in the base unit 102 and the head unit 106 can be facilitated by cables and/or conduits that are routed internally through the robotic arm 104 or externally thereof. For purposes of clarity, these cables and/or conduits are shown as being external of the robotic arm in FIG. 2, but it should be understood that the solution is not limited in this regard.

The robot arm 104 can include a plurality of robot arm actuators 212 which determine a position of articulation members 120 under the control of the robot arm control unit 218. Although not shown in FIG. 1, more or fewer robot arm actuators 212 can be provided in the robotic arm 104 to facilitate movement with respect to each of the articulation members. In some scenarios, the robotic arm can also include a plurality of joint position sensors 214. These position sensors are advantageously associated with the robot arm joints 120. In some scenarios, this position information can be used by the system controller 226 to determine a pose of the robotic arm. As explained below in further detail, this information can be useful for determining an exact location and orientation of the X-ray radiation treatment head 116 relative to an X-ray imaging array 109 panel and/or a person undergoing therapeutic radiation treatment. The robotic arm 104 can also optionally include one or more force sensors 215 for determining or sensing a force exerted on the robotic arm 104. These force sensors can be useful to facilitate position tracking, whereby a position of the robotic arm is automatically adjusted in response to patient movements (such as respiratory movement) which occur during an X-ray treatment session.

Robotic Sculpted Beam X-ray System 100 can be controlled by a computer workstation 234. To facilitate such control, the computer workstation 234 can be configured to communicate with the system controller 226 by means of a suitable high speed data connection. The computer workstation can include an operating system and suitable application software to facilitate the various systems and methods described herein. Computer workstations are well-known in the art and therefore will not be described here in detail. However, it should be noted that the computer workstation can include a computer processor, memory, a display screen (such as display screen 112) which may be a touchscreen, one or more user interface components such as a keyboard, a pointing device (e.g., a mouse), and a network interface component to facilitate communications with the Robotic Sculpted Beam X-ray System 100. In some scenarios, the system 100 can also be operatively coupled to a Sculpted Beam Treatment Planning System ("SBTPS") 236 which is configured to facilitate therapeutic radiation treatment planning.

The SBTPS offers a dedicated method and system to create a real-time treatment plan for the Robotic Sculpted Beam X-ray System. The SBTPS architecture can be comprised of a tablet computing device 237 as the main user interface, a computer workstation which instantiates a parallel processor machine (such as a CUDA®, or other parallel processing platforms and architectures), and the Robotic Beam Sculpting IORT System 100, all operating on a dedicated secured closed-loop Gigabit or faster network. The SBTPS 236 can be configured so that it is capable of creating multiple real time sculpted beam treatment plans for one or more Robotic Sculpted Beam X-ray Systems 100 in a facility. Furthermore, the SBTPS architecture can allow multiple users to work on the same treatment plan simultaneously. Data communications among the system 100, and external computer systems such as the workstation 234 and SBTPS 236 can be facilitated by a network router 232.

The various components comprising the X-ray generating system in Robotic Sculpted Beam X-ray System 100 can be controlled so that they are selectively optimized for a therapeutic radiation treatment operations as hereinafter described. The therapeutic radiation treatment can in some scenarios include IORT interaction with tumor bed tissue, whereby the radiation will have minimal effects at deeper tissue depths. For example, a superficial radiation therapy (SRT) type of X-ray source can be used for this purpose. As will be appreciated, an SRT type of X-ray unit produces low energy X-rays that is suitable for this purpose. In other scenarios, a therapeutic treatment can involve Brachytherapy.

In some scenarios, a solid-state X-ray beam sensor array 108 can be used to capture information concerning an X-ray beam produced by the X-ray source 210. The beam sensor array will be described in detail below. However, it should be noted that the X-ray beam sensor array can be integrated in a balloon applicator which encloses or surrounds the X-ray radiation treatment head 116. In such a scenario, X-ray beam sensor data can be dynamically captured in real-time while therapeutic X-ray treatment is delivered to the patient. The captured X-ray beam sensor data can be communicated to an on-board processing element (such as system controller 226) and/or SBTPS 236) to evaluate beam performance. In particular, the characteristics of the X-ray beam (intensity, shape, duration) can be dynamically compared in real-time to predetermined beam characteristics developed during a radiation therapy planning sessions. In other words, the applied radiation therapy can be actively managed and evaluated to ensure that it is consistent with a predetermined radiation therapy plan. The X-ray beam can be dynamically controlled if needed to more accurately ensure that the therapeutic treatment which is being delivered exactly matches the radiation therapy plan.

The Robotic Sculpted Beam X-ray System 100 is controlled and operated by the system controller 226, which can include a central computer with a motherboard that runs operation and control software that allow it to control, communicate, and monitor the various sub-components and modules of the system 100. This achieves harmonious functionality between the main clinical components of the system 100 including the X-ray generating components (208, 210, 222, 224) and the robotic arm 104.

The system controller 226 can be in communication with a machine-readable medium which can be static memory on which is stored one or more sets of instructions (e.g., software) embodying any one or more of the methodologies or functions described herein, including those methods illustrated herein. The instructions may also reside, completely or at least partially, within the system data repository, static memory, or within the processor, or a combination thereof, during execution thereof by the system 100. The system data repository and patient data repository and the processor also may constitute machine-readable media.

Patient-related data and treatment parameters, such as patient records, treatment session details, and disease documentation and photos can be stored in one or more patient data storage devices 240 which are communicatively coupled to the SBTPS 236. System-related data and parameters, such as the system log, x-ray calibration data, and system diagnostics results can be stored in a data repository 238 associated with workstation 234. The patient data repository and the system data repository can be discrete devices or physically combined. Both data repositories will be mirrored and backed up to a secured and encrypted HIPAA-compliant cloud storage medium.

System Control

Figure 3:
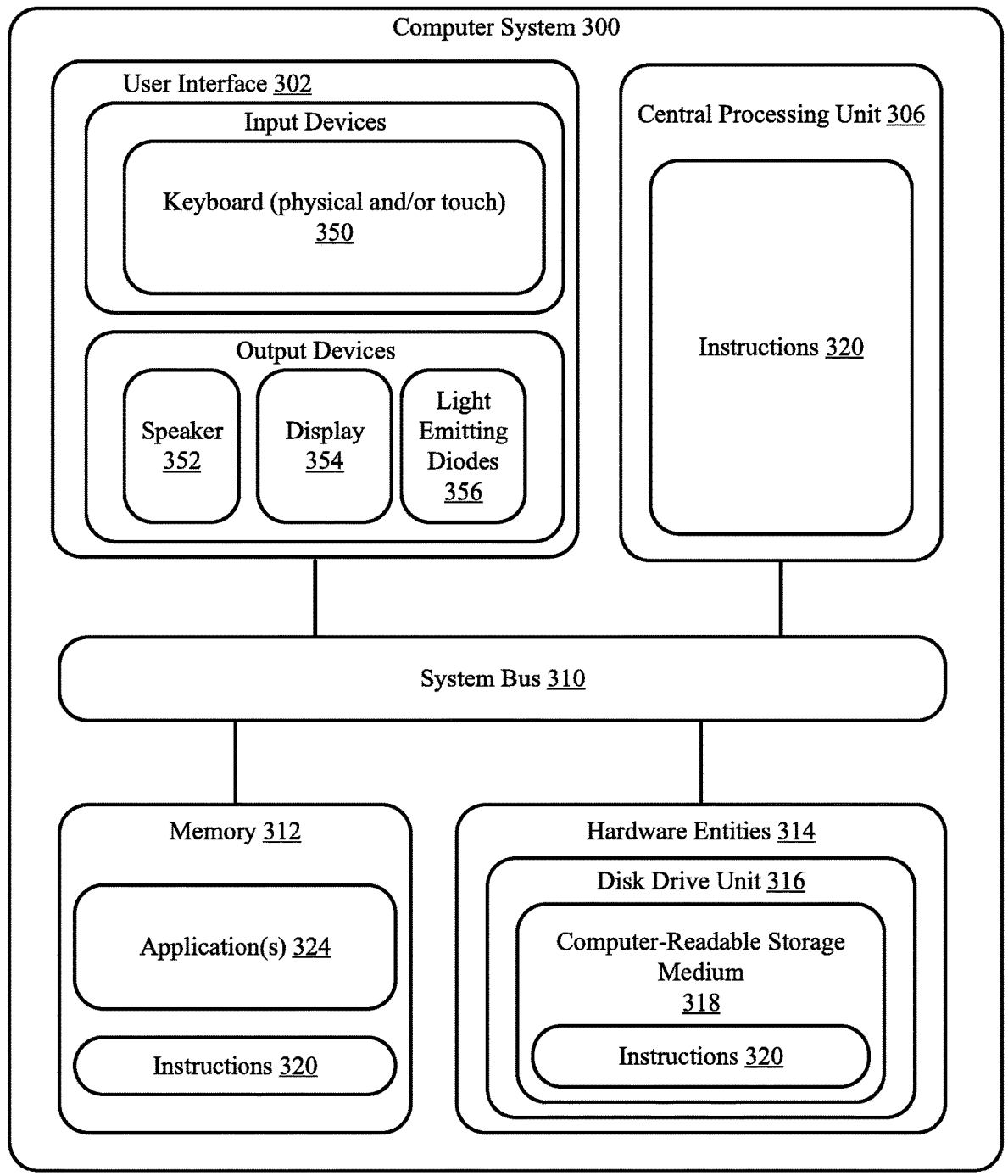
FIG. 3 is a block diagram which is useful for understanding certain aspects of a control system which can be used to perform certain processing operations of associated with a robotic X-ray system as described herein.

Referring now to FIG. 3, there is provided an illustration of an exemplary computer system 300. The exemplary computer system 300 is sufficient to understand a computer system associated with the system controller 226 for controlling a Robotic Sculpted Beam X-ray System 100 as described herein. The exemplary computer system 300 is also sufficient to understand an exemplary architecture associated with an SBTPS 236 and the computer workstation 234.

The computer system 300 can include, but is not limited to, machines (or computing devices) running a suitable operating system (e.g. Windows OS, Linux, Apple Mac OS or other type of operating system now known or known in the future). Such machines (or computing devices) are well known in the art, and will not be described in detail herein. Still, it should be understood that such machines are modified to implement all or a portion of the methods described herein. Such modifications can include software modifications, hardware modification or a combination of both.

Computer system 300 may include more or less components than those shown in FIG. 3. However, the components shown are sufficient to disclose an illustrative embodiment implementing the present solution. The hardware architecture of FIG. 3 represents one embodiment of a representative computing device configured to facilitate the operations described herein.

Some or all the components of the computer system 300 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 3, the computer system 300 comprises a user interface 302, a Central Processing Unit ("CPU") 306, a system bus 310, a memory 312 connected to and accessible by other portions of computing device 300 through system bus 310, and hardware entities 314 connected to system bus 310. The user interface can include input devices and output devices, which facilitate user-software interactions for controlling operations of the computing device 300. The input devices include, but are not limited, a physical and/or touch keyboard 350. The input devices can be connected to the computing device 300 via a wired or wireless connection (e.g., a Bluetooth® connection). The output devices include, but are not limited to, a speaker 352, a display 354, and/or light emitting diodes 356.

At least some of the hardware entities 314 perform actions involving access to and use of memory 312, which can be a Radom Access Memory ("RAM"), a disk drive and/or a Compact Disc Read Only Memory ("CD-ROM"). Hardware entities 314 can include a disk drive unit 316 comprising a computer-readable storage medium 318 on which is stored one or more sets of instructions 320 (e.g., software code) configured to implement one or more of the methodologies, procedures, or functions described herein. The instructions 320 can also reside, completely or at least partially, within the memory 312 and/or within the CPU 306 during execution thereof by the computing device 300. The memory 312 and the CPU 306 also can constitute machine-readable media. The term "machine-readable media", as used here, refers to a single medium or multiple media (e.g., a centralized or distributed database, and/or associated caches and servers) that store the one or more sets of instructions 320. The term "machine-readable media", as used here, also refers to any medium that is capable of storing, encoding or carrying a set of instructions 320 for execution by the computer system 300 and that cause the computer system 300 to perform any one or more of the methodologies of the present disclosure.

Steered Beam X-ray Source

Turning now to FIGS. 4A and 4B there is shown one example of an X-ray source 400 which can be used with the robotic X-ray system described herein. This type of X-ray source is described in detail in U.S. patent application Ser. No. 15/941,547, filed Mar. 30, 2018, entitled Three-Dimensional Beam Forming X-ray Source, the disclosure of which is incorporated herein by reference. Briefly, the system comprises an electron beam gun (EBG) 402 and a drift tube 404 which is supported on an end of the robotic arm distal from the base. The EBG can comprise an ion pump (such as ion pump 208). An X-ray generating element 422 resides at an end of the drift tube 404, distal from the EBG. In some scenarios, the EBG 402 can reside in a head unit 106 as described herein. For example, the EBG 402 can reside in the head unit 106, attached to a robotic arm 104. In such a scenario, the elongated applicator body 118 can be comprised of the drift tube 404. Further, the treatment head 116 can be comprised of the X-ray generating element 422. A fiducial marker 449 can be disposed in the head unit 106.

The drift tube 404 is comprised of a conductive material such as stainless steel. Alternatively, the drift tube can be comprised of a ceramic material such as alumina or aluminum nitride with a conductive inner lining. The hollow inner portion of the drift tube is maintained at a vacuum pressure (e.g. a suitable vacuum pressure for purposes of embodiments described herein can be in the range below about 10–5 torr or particularly between about $10^{-9}$ torr to $10^{-7}$ torr).

The X-ray generating element 422 is comprised of a directionally controlled target assembly (DCTA) 426. The DCTA includes an X-ray target 432 and a beam shield 434 (which is also sometimes referred to herein as a scepter). In the X-ray source shown in FIG. 4A, electrons e generated by an ion pump 208 form an electron beam 454 as they are accelerated by the EBG toward the X-ray target 432. These electrons will have significant momentum when they arrive at the entry aperture of the drift tube. At least the inner lining of the drift tube is maintained at ground potential. Accordingly, the momentum imparted to the electrons by EBG 402 will continue to ballistically carry the electrons down the length of the drift tube at very high velocity (e.g. a velocity approaching the speed of light) toward the X-ray target 432. It will be appreciated that as the electrons are traveling along the length of the drift tube 404, they are no longer electrostatically accelerated. When the electrons impact upon the X-ray target 432, X-rays are generated.

The direction and shape of the X-ray beam produced by X-ray source 400 can be sculpted or varied by using electromagnetic steering coils 405. The steering coils 405 are under the control of beam steering coil control 224 provided in the base unit. The steering coils 405 are configured to vary which portion of the X-ray target 432 is impacted by the electrons that comprise the electron beam. This steering process can be facilitated by the beam shield 434 which is disposed adjacent to the X-ray target 432. For example, in some scenarios, the X-ray source can be dynamically configured or controlled so as to facilitate a substantially isotropic pattern 500 for x-ray photon particles as shown in FIG. 5. In other scenarios, the X-ray source can be selectively controlled to instead facilitate a directional X-ray beam 502 as shown in FIG. 6. In FIGS. 5 and 6, examples of beam vector directions 504 are shown extending from the X-ray radiation source 400.

As best understood with reference to FIG. 4B, the X-ray target 432 is comprised of a disk-shaped element which is disposed transverse to a direction of travel associated with the electron beam 454. For example, in some scenarios the disk-shaped element can be disposed in a plane which is approximately orthogonal to the direction of electron beam travel.

In some embodiments, the X-ray target 432 can enclose an end portion of the drift tube distal from the EBG 402 to facilitate maintenance of the vacuum pressure within the drift tube. The X-ray target 432 can be almost any material, however it is advantageously comprised of a material such as molybdenum, gold, or tungsten which has a high atomic number so as to facilitate the production of X-rays at relatively high efficiency when bombarded with electrons. The generation of X-rays at X-ray target 432 can generate substantial amounts of heat. So a flow of coolant provided by the water cooling system (206) can be provided to the treatment head through coolant conduits 406. The various components comprising the X-ray source 400 (e.g., EBG 402, the drift tube 404, and X-ray generating element 422) can be mounted on the robotic arm 104 as shown in FIGS. 1 and 2.

As shown in FIG. 4B, the beam shield 434 can include a first portion 436 which is disposed adjacent to one major surface of the target 432, and a second portion 438, which is disposed adjacent to an opposing major surface of the target. In some scenarios, the first portion 436 can be disposed internal of the drift tube 404 within a vacuum environment, and the second portion 438 can be disposed external of the drift tube. If a portion of the beam shield 434 is disposed external of the drift tube as shown in FIG. 4B, then an X-ray-transmissive cap member 448 can be disposed over the second portion 438 of the beam shield to enclose and protect the portions of the DCTA external of the drift tube.

The beam shield or scepter 434 is comprised of a plurality of wall elements 440, 442. The wall elements 442 associated with the first portion 436 can extend from a first major surface of the disk-shaped target which faces in a direction toward the EBG 402. The wall shaped elements 440 associated with the second portion 438 can extend from the opposing major surface of the target facing away from the EBG 102. The wall elements 440, 442 also extend in a radial direction outwardly from a DCTA centerline 446 toward a periphery of the disk-shaped target 432. Accordingly, the wall elements form a plurality of shielded compartments 450, 452. The wall elements 440, 442 can be advantageously comprised of a material which interacts in a substantial way with X-ray photons. In some scenarios, the material can be one that interacts with the X-ray photons in a way which causes the X-ray photons to give up a substantial part of its energy and momentum. Accordingly, one type of suitably interactive material for this purpose can comprise a material that attenuates or absorbs X-ray energy. In some scenarios, the material chosen for this purpose can be advantageously chosen to be one that is highly absorbent of X-ray energy.

Suitable materials which are highly absorptive of X-ray radiation are well known. For example, these materials can include certain metals such as stainless steel, molybdenum (Mo), tungsten (W), tantalum (Ta), or other high atomic number (high-Z) materials. As used herein the phrase high-Z material will generally include those which have an atomic number of at least 21. Of course, there may be some scenarios in which a lesser degree of X-ray absorption is desired. In such scenarios, a different material may be suitable. Accordingly, a suitable material for the shield wall is not necessarily limited to high atomic number materials.

In the scenario shown in FIG. 4B, the plurality of wall elements extend radially outward from the centerline 446. However, the configuration of the beam shield is not limited in this regard and it should be understood that other beam shield configurations are also possible. Each of the wall elements can further comprise rounded or chamfered corners 441 to facilitate beam formation as described below. These rounded or chamfered corners can be disposed at portions of the wall elements, which are distal from the X-ray target 432 and spaced apart from the centerline 446.

As shown in FIG. 4B, wall elements 440 can be aligned with wall elements 442 to form aligned pairs of shielded compartments 450, 452 on opposing sides of the target 432. Each such shielded compartment will be associated with a corresponding target segment 444 which is bounded by a pair of wall elements 440 on one side of the X-ray target 432, and a pair of wall elements 442 on an opposing side of the target.

As is known, X-ray photons are released in directions which are generally transverse to the collision path of the electron beam with the major surface of the X-ray target 432. The material of the X-ray target is comprised of a relatively thin layer of target material such that electrons bombarding the X-ray target 432 produce X-rays in directions extending away from both major surfaces of the target. Each aligned pair of shielded compartments 450, 452 (as defined by wall elements 440, 442) and their corresponding target segment 444 comprise a beam-former. X-rays which are generated when high energy electrons interact with a particular target segment 444 will be limited in their direction of travel by the wall elements defining the compartments 450, 452. This concept is illustrated in FIG. 4B, which shows that an electron beam 454 bombards a segment of target 432 to produce transmitted and reflected X-rays in directions that are generally transverse to the collision path of the electron beam 454. But it can be observed in FIG. 4B that the X-rays will only be transmitted over a limited range of azimuth and elevation angles $\alpha$, $\beta$ due to the shielding effect of the beam-former. By selectively controlling which target segment 444 is bombarded with electrons, and where within the target segment 444 that the electron beam actually strikes the target segment, the X-ray beams in a range of different directions and shapes can be selectively formed and sculpted as needed.

Accordingly, the X-ray beam direction (which is defined by a main axis of transmitted X-ray energy), and a pattern of relative X-ray intensity, which comprises the shape of the beam, can be selectively varied or controlled to facilitate different treatment plans. The exact three-dimensional shape or relative intensity pattern of the X-ray beam will vary in accordance with several factors described herein. In some scenarios, the electron beam can be rapidly steered so that different target segments 444 are successively bombarded with electrons so that the electron beam intersects different target segments for predetermined dwell times. If more than one target segment 444 is bombarded by the electron beam in this way, then multiple beam segments can be formed in selected directions defined by the associated beam-formers and each can have a different beam shape or pattern. The total intensity of the X-ray radiation associated with each beam segment is approximately proportional to the square of the electron beam accelerating voltage applied by the EBG. So, in some scenarios, the intensity of an X-ray beam associated with each of the multiple beam segments can be respectively controlled by selectively controlling a voltage potential of an EBG cathode relative to the anode.

The multiple beam segments are composite elements of the overall X-ray beam that is produced by the DCTA. So by controlling the location where the electron beam intersects each beam segment, the dwell or duration of time that the beam is allowed to intersect each target element, and the energy level of the electron beam during each dwell time, the system can create practically any composite X-ray beam pattern. This process is sometimes referred to herein as beam sculpting and is a function of the manner in which the electron beam is applied to the X-ray target with respect to geometry, energy and time. So controlling electron beam geometry, energy and time (GET) with respect to the DCTA allows complete control of the resulting composite X-ray beam to facilitate a desired radiation treatment plan. Further, beam intensity in certain radial or azimuth directions with respect to the central axis 446 can be reduced to substantially zero. In other words, the X-ray beam in a particular radial or azimuth direction can be essentially disabled to facilitate a particular radiation treatment plan. Control over the beam generators can be facilitated by a control system (such as system controller 226).

Therapeutic Treatment Operations

Figure 7:
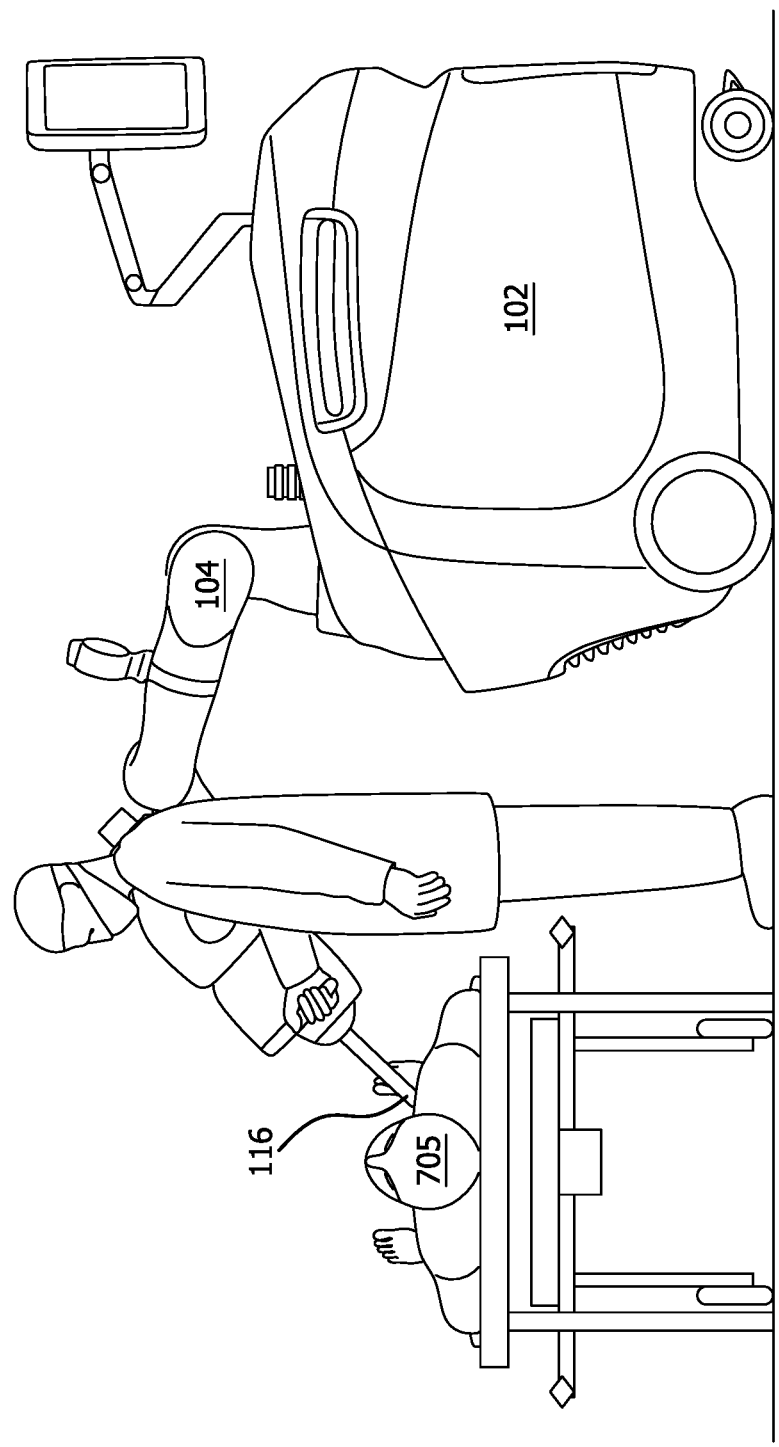
FIG. 7 is a drawing which is useful for understanding how the X-ray system in FIGS. 4A and 4B can be used in the robotic X-ray system of FIG. 1.

The Robotic Sculpted Beam X-ray System 100 is multi-functional insofar as it can be used to perform therapeutic treatment such as IORT, Brachytherapy, and External Beam Radio Therapy (EBRT). For example, consider an IORT scenario in which a surgical procedure has been performed to remove a cancerous tumor from a patient. This IORT procedure is illustrated in FIG. 7 which shows the surgeon can use the robotic arm 104 to reposition the X-ray treatment head 116 with respect to the subject patient 705. In particular, the X-ray source can be repositioned within a tumor bed of the removed cancerous tumor. Thereafter, the X-ray source can be activated while the treatment head 116 is disposed at the treatment location so as to carry out a therapeutic X-ray treatment of the subject patient.

Treatment Planning

The Sculpted Beam Treatment Planning System ("SBTPS") 236 offers a dedicated method and system to create a real-time treatment plan for the Robotic Sculpted Beam X-ray System 100. The SBTPS is capable of creating multiple real time sculpted beam treatment plans for one or more Robotic Sculpted Beam X-ray Systems 100 in a facility. Furthermore, the SBTPS architecture can allow multiple users to work on the same treatment plan simultaneously.

Figure 8:
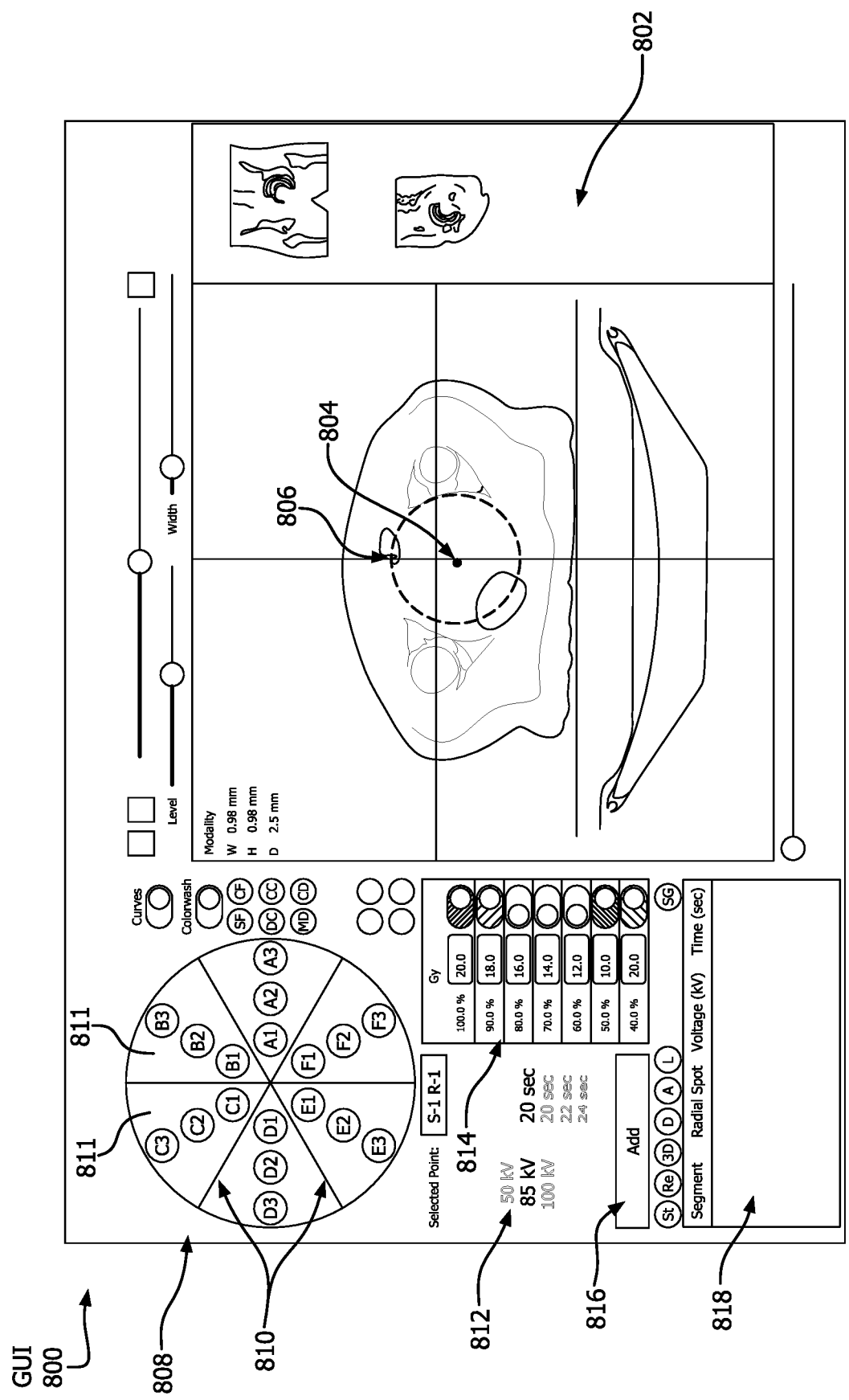
FIGS. 8-9 each provide a screen shot of an illustrative Graphical User Interface ("GUI") for creating a treatment plan for a patient.

Referring now to FIG. 8, there is provided a screen shot of an illustrative GUI 800 provided by a software application associated with the SBTPS 236. GUI 800 is designed to facilitate the creation of a treatment plan for a patient who is to have radiation therapy in relation to his/her cancer. In this regard, the GUI comprises a first portion 802 showing medical imaging scans of the patient's abdomen. In some scenarios, the imaging scan may be a CT scan acquired following the removal of a tumor. In some scenarios, the imaging scan can be facilitated by using the system 100 so that the same device used for X-ray treatment can also be used to facilitate the medical imaging needed to facilitate such treatment. A location of a fiducial marker (e.g., fiducial marker 449) can be shown within the image by the presence of a dot 804. This fiducial marker allows the user to know within the context of the scan where the treatment head 116 resides inside the patient. A balloon applicator which surrounds the treatment head resides in the area encompassed by the dotted line 806. The balloon applicator is discussed in detail below.

Figure 9:
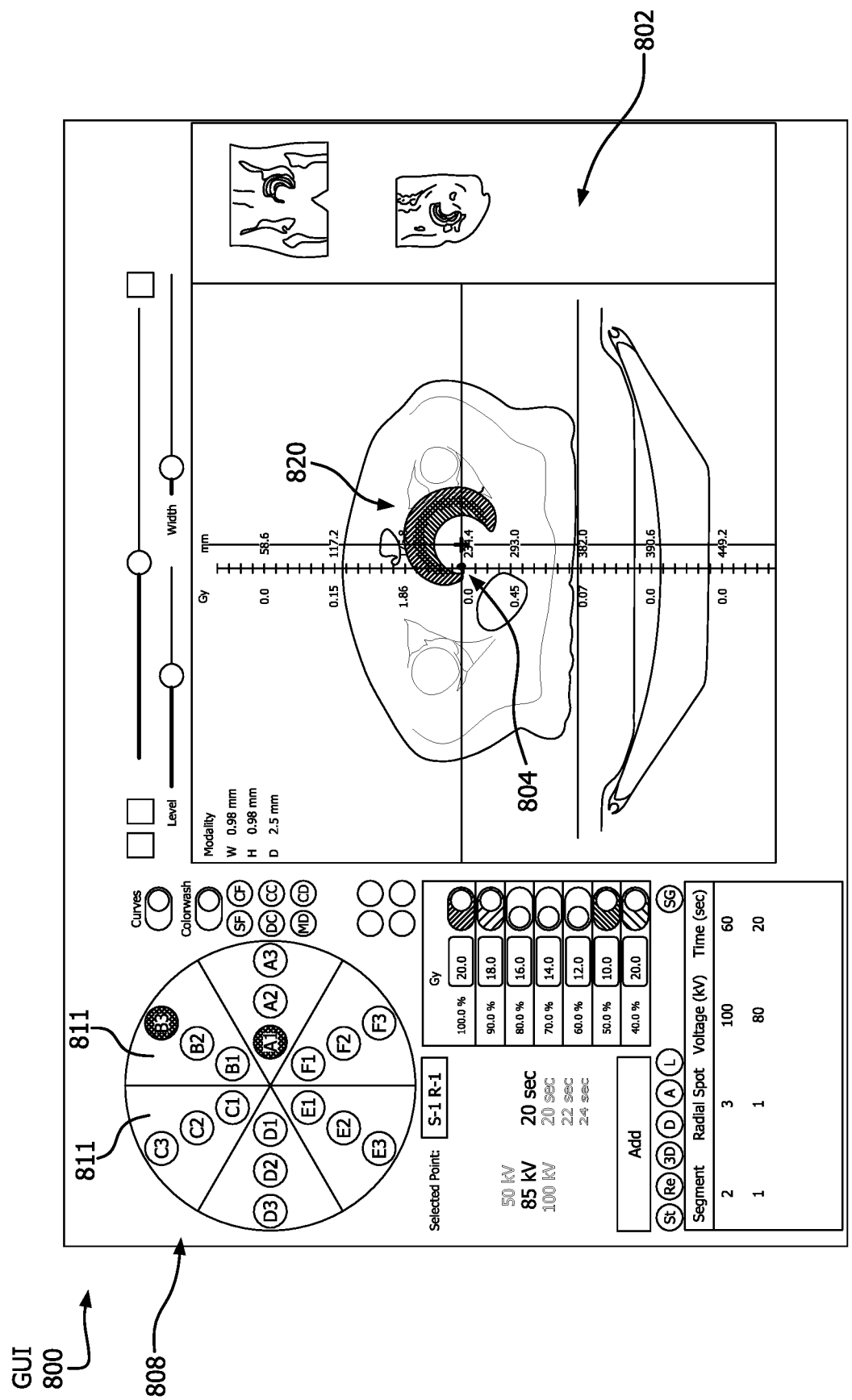

As noted above, a DCTA 426 which resides within the treatment head 116 has a plurality of compartments 450, 452 from which X-ray radiation can be emitted. A schematic illustration of the treatment head and its compartments is provided in a second portion 808 of the GUI 800. As shown in portion 808, schematic representations of electron beam target segments 811 (corresponding to target segments 444) are shown in association with each compartment. Each of these target segments are marked with target locations designated A1-A3, B1-B3, C1-C3, D1-D3, E1-E3 and F1-F3. Wall elements 440, 442 which define the compartments are represented by lines 810. The electron beam target areas marked A1-A3, B1-B3, C1-C3, D1-D3, E1-E3 and F1-F3 can be selected by a user to facilitate formation of a desired X-ray beam. The GUI 800 also comprises widgets 812-816 which allow the user to select an intensity of radiation to be applied to the patient, and a duration at which radiation should be applied to the patient. By depressing the virtual button 816, a treatment item is added to the treatment plan shown in a third portion 818 of the GUI. Once the treatment plan has been created, the system controller 226 of Robotic Sculpted Beam X-ray System 100 can be programmed to apply radiation to the patient in accordance with the same. An example of an X-ray radiation pattern 820 for an exemplary treatment plan is shown in FIG. 9.

In some scenarios, automated beam sculpting can be facilitated by the SBTPS 236 as hereinafter described. A user can start the treatment planning process by selecting a patient from a patient roster. The user can now either select a pre-created treatment plan, or start a new treatment plan. If there is a pre-created treatment plan, it may be either approved or just pending. If the treatment plan is approved, it is locked and set for treatment and the user cannot edit it, but only load and send it to the Robotic Beam Sculpting IORT System. If the treatment plan is in Pending status, the user can open and edit it in order to complete and approve it for treatment.

When the user initiates a new treatment plan, the system will load the Treatment Planning environment. The Treatment Planning environment provides the user with anatomical imaging of a patient as shown in FIGS. 8 and 9. The user can change the window level (contrast and brightness) of the displayed image, scroll through the imaging data's slices, and triangulate the anatomical display, by selecting a certain area of anatomy, and the system will display the corresponding viewing planes of the selected area in the anatomy (sagittal, axial, and coronal).

The system also provides the function of zooming in and out of any displayed plane for any selected and viewed slice. The system also displays the various anatomical image parameters on the main image view. The image parameters include, but not limited to, voxel width, height, and depth, image size in pixels and metric units (size per pixel), the zoom rate, the location of the selected triangulation spot, the selected slice index number, and the relative view depth in the patient anatomy. The system also displays the dose rate spectrum on the corner of the main anatomical image display, as a reference guide and baseline for the user.

Once the desired anatomical region and view mode have been selected, the user locates and selects the fiducial marker's location 804 in the anatomy by double-clicking (or other pointing methods and devices) on the desired location. The fiducial markers can be embedded in the treatment head and/or a balloon applicator described below so that they may be identified using the imaging modality (CT, MRI, or PET/CT, for example). The fiducial marker selection may include one or more fiducial markers, as required and available for the treatment plan.

In some scenarios, the user can mark the contours of a designated treatment area. The contours marking process may be graphical and done by either a pointing device, such as a stylus, trackball, or mouse, or finger (on the mobile device's touch display). The contours are marked twice in each displayed anatomical image slice—max and min. The max contour designates the area where the maximal dose should be deposited, and the min contour designates the lowest dose deposition. Both max and min thresholds can be adjusted on the system through the GUI. The user repeats this operation at every slice in order to cover the entire treatment volume. The system registers every contouring and other user action on the main display slice throughout all anatomical planes.

Once the contouring creation process is complete, the user initiates a Beam Sculpting Engine Parallel Processor (BSEPP) simulator associated with the SBTPS 236. The BSEPP computes and picks the most optimal treatment plan for the selected geometry and topology of the patient's designated anatomy to be treated. The complete treatment plan and volume that is derived from the drawn contours on the system. The BSEPP also calculated and displays the total dwell time of the x-ray source in a given physical location.

The BSEPP runs an iterative computational cycle to optimize the planned sculpted beam's geometry and volume in the most accurate manner to conform with the user's desired max and min contours and anatomical volume. The BSEPP then generates the final treatment plan and beam firing sequence to include target segment index/location (geometry), energy, and time (GET). These three parameters comprise the system's Target Sculpting Factor (TSFs). The computed treatment plan is then rendered and fused in the three plane views of the patient's anatomy. The system displays the computed sculpted beam embedded in the patient's anatomy volume with the isodose color wash superimposed with the user's drawn min/max contours. The user has the ability to toggle between a color wash, isodose curves contour, or multiple display of both elements, or turn them off altogether.

Once the BSEPP completes the sculpted beam treatment plan, the user can review and validate it with the system's rendered simulation display. The user at this juncture, can edit and modify the plan as required. The system allows the user to modify the firing sequence of the electron beam of the X-ray source, manually change the Target Sculpting Factor (TSF), which includes the target segment index, the hit position within the segment (innermost [TM], medial [M], and outermost [OM]), energy (in kV), and dwell time (in seconds), and the x-ray source's translation rate.

Once the treatment plan is complete, the user can either approve the plan for a later use, or directly approve and load the treatment plan to the Robotic Sculpted Beam X-ray System for immediate treatment delivery.

Treatment Verification

When the Robotic Sculpted Beam X-ray System 100 is fully calibrated and functioning properly, the sculpted beam produced by an X-ray generating element 922 should correspond to the prescribed treatment plan. Consequently, the duration, intensity and locations where X-ray energy is delivered to the patient should be entirely consistent with the treatment plan. However, dynamic real-time monitoring of the actual X-ray treatment can help to ensure that the therapeutic treatment that is actually applied to the patient treatment is actually consistent with the prescribed treatment plan.

Accordingly, a treatment verification solution is provided whereby real-time monitoring of X-ray dosimetry is facilitated. The solution involves the uses of an X-ray beam sensor array 108 which includes a plurality of X-ray radiation sensor elements (XRSE). These XRSE are disposed on the surface of (or integrated in) a balloon applicator. The XRSE are configured to communicate the result of their sensing activities in real time to a control system (e.g., system controller 226). The control system monitors the X-ray radiation dose detected by each of the sensors and compares the dose at each location to an expected dose in accordance with a radiation treatment plan.

Figure 10:
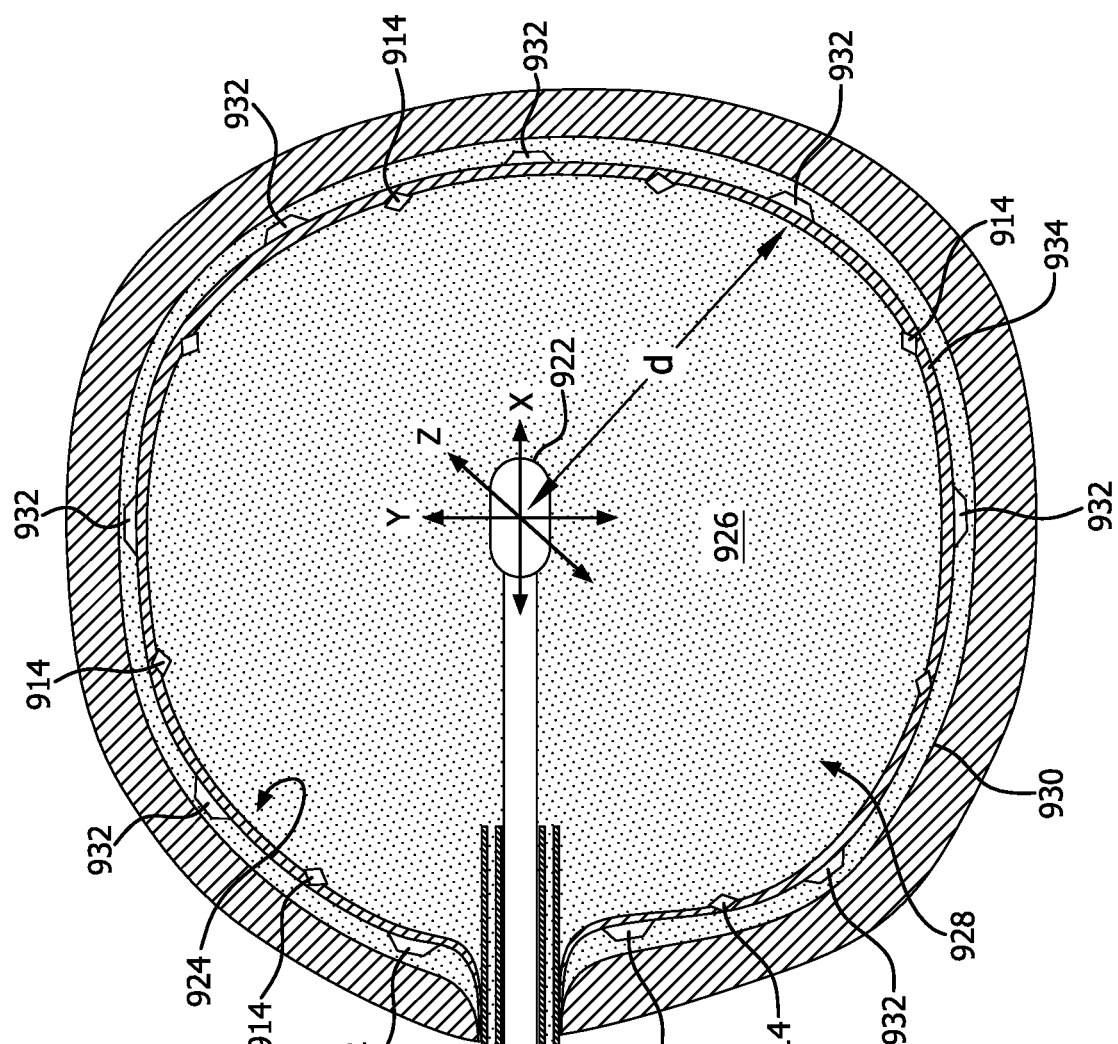
FIG. 10 is a drawing that is useful for understanding an arrangement of X-ray dosimetry sensors disposed on a balloon applicator of an X-ray system.

Shown in FIG. 10 is a balloon applicator 924 which can be used with an X-ray source in a Robotic Sculpted Beam X-ray System 100 described herein. The balloon applicator 924 has an ovoid or spherical shape and can be formed of a material such as Nylon, Pebax, PET, or polyurethane. Further the balloon applicator material can be comprised of a blends and/or compositions of such materials. For example, a single layer, dual layers or multiple layers of such materials are possible. The balloon applicator material(s) is advantageously selected so that it is radiolucent with respect to the range of X-ray radiation to be applied. In some scenarios, the balloon applicator 924 can be comprised of an elastic material. Accordingly, when inflated with a fluid 926, such as saline, the balloon applicator will expand to fill an interstitial space 928 between the X-ray source and a tissue wall 930 (e.g. a tissue wall comprising a tumor bed). Fluid conduits 910, 912 can facilitate a flow of fluid to and from the interior of the balloon applicator.

Figure 11:
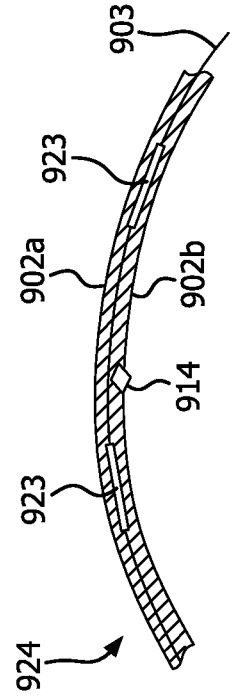
FIG. 11 is a drawing that is useful for understanding an X-ray sensor which is integrated within a material or material layers comprising a balloon applicator of an X-ray system.

A plurality of X-ray radiation sensor elements (XRSE) 932 are disposed on a surface 934 of the balloon applicator 924. This surface can be an external or internal surface of the balloon applicator. However, positioning the XRSE on an external surface can be advantageous to ensure that the XRSE are not exposed to saline or other liquids used to inflate the balloon applicator. In an alternative embodiment shown in FIG. 11, the XRSE 923 can be integrated within or disposed between one or more layers comprising the balloon applicator.

The XRSE 932 can be disposed at a plurality of predetermined locations in or on the surface of the balloon applicator. In some scenarios, these locations can be aligned with each of a plurality of orthogonal axis as shown which define an x, y and z coordinate system. In such a scenario, the X-ray radiation source associated with the X-ray generating element 922 can be generally aligned at the origin where the orthogonal axis intersect. In other scenarios, the plurality of XRSE 932 can be aligned with a plurality of points which define an ovoid or roughly spherical grid formed on the surface of the balloon applicator. The term ovoid or spherical grid as used herein can be a set of points which are uniformly (or semi-uniformly) disposed over the surface of an ovoid or approximately spherical shape as defined by the balloon applicator.

It will be appreciated that a balloon applicator 924 which surrounds an X-ray generating element 922 can be inflated to varying degrees. In such scenarios, the positions of the XRSE relative to the X-ray generating element 922 will necessarily change for different inflation volumes/pressure. But the actual locations and distance d between the X-ray source and each XRSE can be known by employing various measures. For example, in one scenario an amount of saline pumped into the balloon, and/or saline pressure within the balloon applicator can be carefully controlled. Empirical measurements can then be conducted to determine the resulting distance from the XRSE to the X-ray generating element under various inflation conditions. Alternatively, the characteristics of the balloon can be modeled using computer software so that the radius of the inflated balloon applicator is known for different inflation conditions. Consequently, it is possible to determine an approximate distance between a position of the XRSE and the X-ray generating element 922 under various conditions of balloon applicator inflation.

In other scenarios, the inflation characteristics of the balloon applicator and/or the position of the XRSE, can be evaluated by utilizing a plurality of fiducial markers 914. The fiducial markers 914 can be attached to or embedded in a material which forms the surface of the balloon applicator. These fiducial markers can be detected with conventional medical imaging so that a contoured shape and size of the balloon applicator may be understood in advance of the therapeutic radiation treatment. The use of fiducial markers in this manner can be advantageous when the shape of a tumor wound cavity prevents the balloon applicator from inflating to a substantial spherical shape. The fiducial markers can define the shape of the balloon applicator (and the associated locations of the XRSE) even under conditions where the inflated balloon applicator has an irregular shape. In some scenarios, the fiducial markers 914 can be co-located with the XRSE 932 so that the exact location of the XRSE will be indicated by the fiducial marker.

Figure 12:
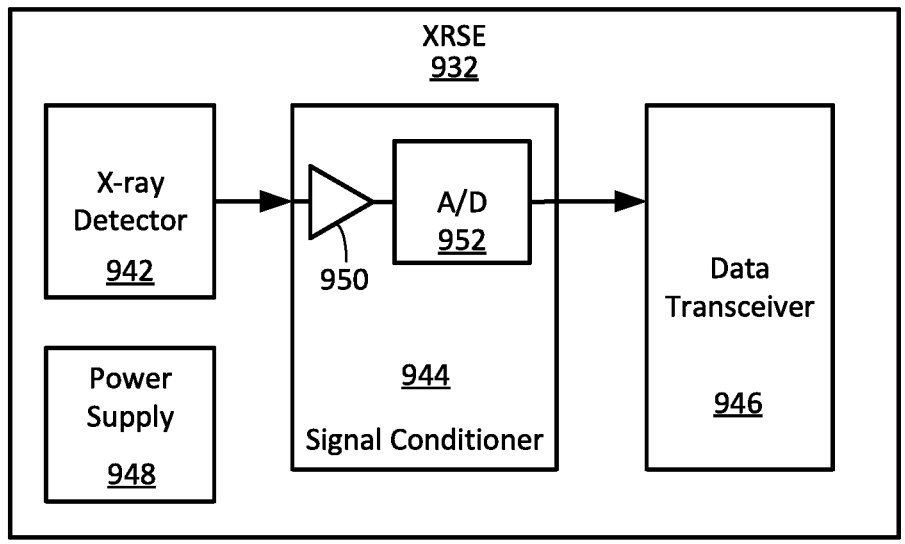
FIG. 12 is a block diagram that is useful for understanding an X-ray sensing element.

FIG. 12 is a block diagram which is useful for understanding an example architecture of an XRSE 932. The XRSE can comprise an X-ray detector 942, a signal conditioner 944, and a data transceiver 946. The X-ray detector 942 can comprise any suitable type of X-ray sensing technology. For example, the X-ray detector can be comprised of solid state semiconductor materials (e.g., based around silicon or germanium chips), silicon drift detectors (SDD), or PIN diode detectors. PIN diode detectors have the advantage of utilizing a much smaller detector element as compared to other types of X-ray detection devices. Solid state X-ray detectors are well-known in the art and will not be described here in detail. However, it should be noted that there are various types of semiconductor materials which can be used for implementing solid state X-ray detectors. For example, such materials include without limitation silicon (Si), germanium (Ge), and cadmium telluride (CdTe). X-ray photons which are incident on the semiconductor will interact with the material to produce electron-hole pairs. The electron-hole pairs which are produced will increase proportionally with radiation intensity. Accordingly, the electron hole pairs can generate an electric signal to indicate the intensity of the X-ray radiation.

Figure 13:
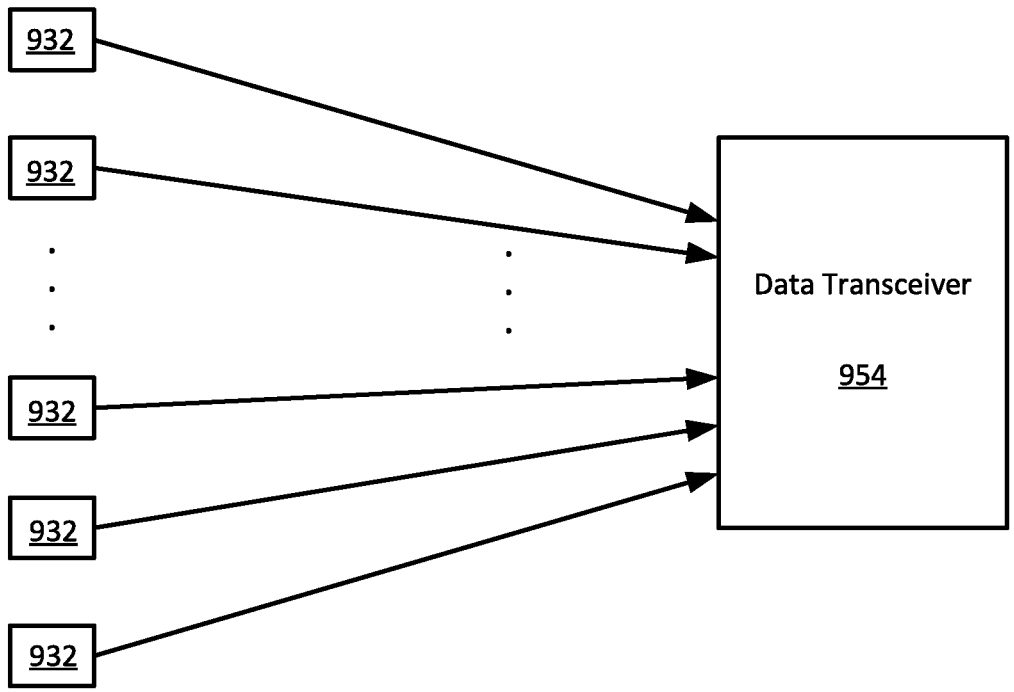
FIG. 13 is a block diagram that is useful for understanding a data communication network involving a plurality of X-ray sensing elements and a data transceiver.

The signal conditioner 944 can comprise a signal buffer and/or amplifier 950, and an analog to digital (A/D) converter 952. The A/D converter is configured to convert analog output signals from the X-ray detector 942 to digital data that is suitable for transmission using the data transceiver 946. The data transceiver 946 can be a wired or wireless type of data transceiver. Each of the XRSE can have a specific logical address for data communications to and/or from the control system transceiver. These communications are conceptually illustrated in FIG. 13 which shows a plurality of XRSE 932 communicating with a control system data transceiver 954.

Figure 14:
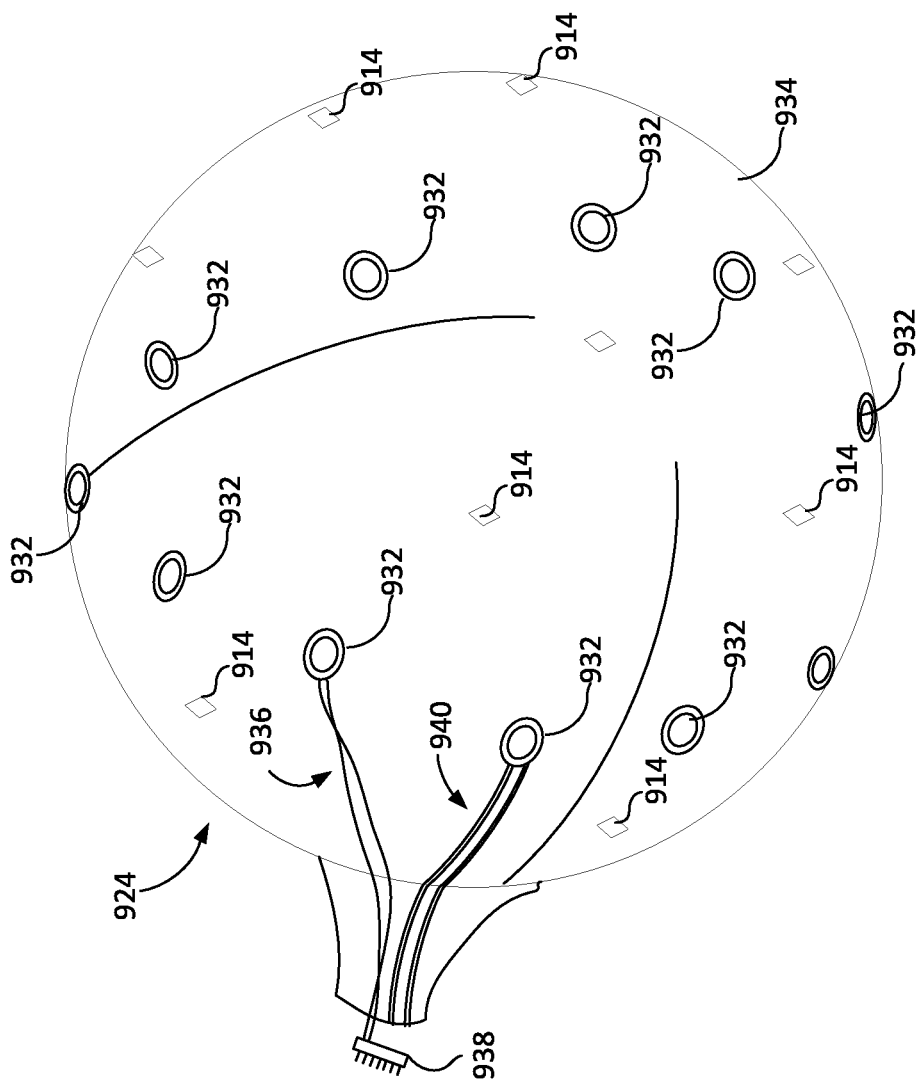
FIG. 14 is a drawing that is useful for understanding how power and/or signal communications can be facilitated between a plurality of XRSE 932 and a data transceiver associated with a control system using conductive wire leads

In some scenarios, power and/or signal communications between the plurality of XRSE 932 and the control system can be facilitated by wired or optical means. FIG. 14 illustrates a scenario in which conductive wire leads or optical fiber can be used to facilitate such functions. These communication/power leads 936 can extend from each XRSE 932 to a suitable connector 938 through which the signals from each XRSE data transceiver can be communicated to the control system data transceiver 954. In some scenarios, the signal communication/power leads can be separate from the balloon applicator. However, in other scenarios, communications/power leads 940 can be integrated in or disposed directly on the surface of the balloon using printed circuit methods. In such scenarios, the leads can be fixed to the outer surface of the balloon as shown in FIG. 14. Alternatively, leads (e.g., power/communication leads 903) can be integrated with or disposed within material layers (e.g. between material layers 902a, 902b) forming the balloon applicator. In some cases, the power/communication leads can be formed of a material which flexes or stretches with the surface of the balloon so that the communication/power leads remain intact as the balloon expands and contracts.

In other scenarios, one or more XRSE can use wireless transceivers to communicate X-ray sensing data from the XRSE to the control system. The wireless transceivers contemplated for this purpose can operate in accordance with any of a variety of well-known wireless communication standards. For example, in some scenarios Bluetooth® or Near Field Communication protocols can be used to facilitate such communications. In a wireless configuration, the power supply 948 used to provide power to the XRSE can be any suitable source of electrical power to support the operations of the XRSE. In some scenarios, the power supply can comprise a battery. In other scenarios, the power supply can include energy harvesting technology to derive power from the X-ray energy emanating from the X-ray source to power the XRSE.

The sensor outputs from the XRSE can be communicated to the system controller 226. Here, the information can be used to model in real-time an X-ray beam produced by the X-ray generating element 922. The information can also be used to determine a radiation dose delivered to tissues at various locations surrounding the balloon applicator.

In an alternative embodiment balloon applicator, the XRSE can be simple passive elements. As is known, when certain materials are exposed to X-ray radiation, ionization will occur which involves the ejection of one or more electrons from atoms which comprise the material. The ejection of an electron in this way results in instability of the electronic structure, thereby causing electrons in higher orbitals to "fall" into lower orbits. This activity releases energy in the form of a photon. Thus, optical radiation is emitted from the material which has specific characteristic energy that is determined in accordance with the type of material. The activity described herein is commonly referred to as fluorescence.

Figure 15:
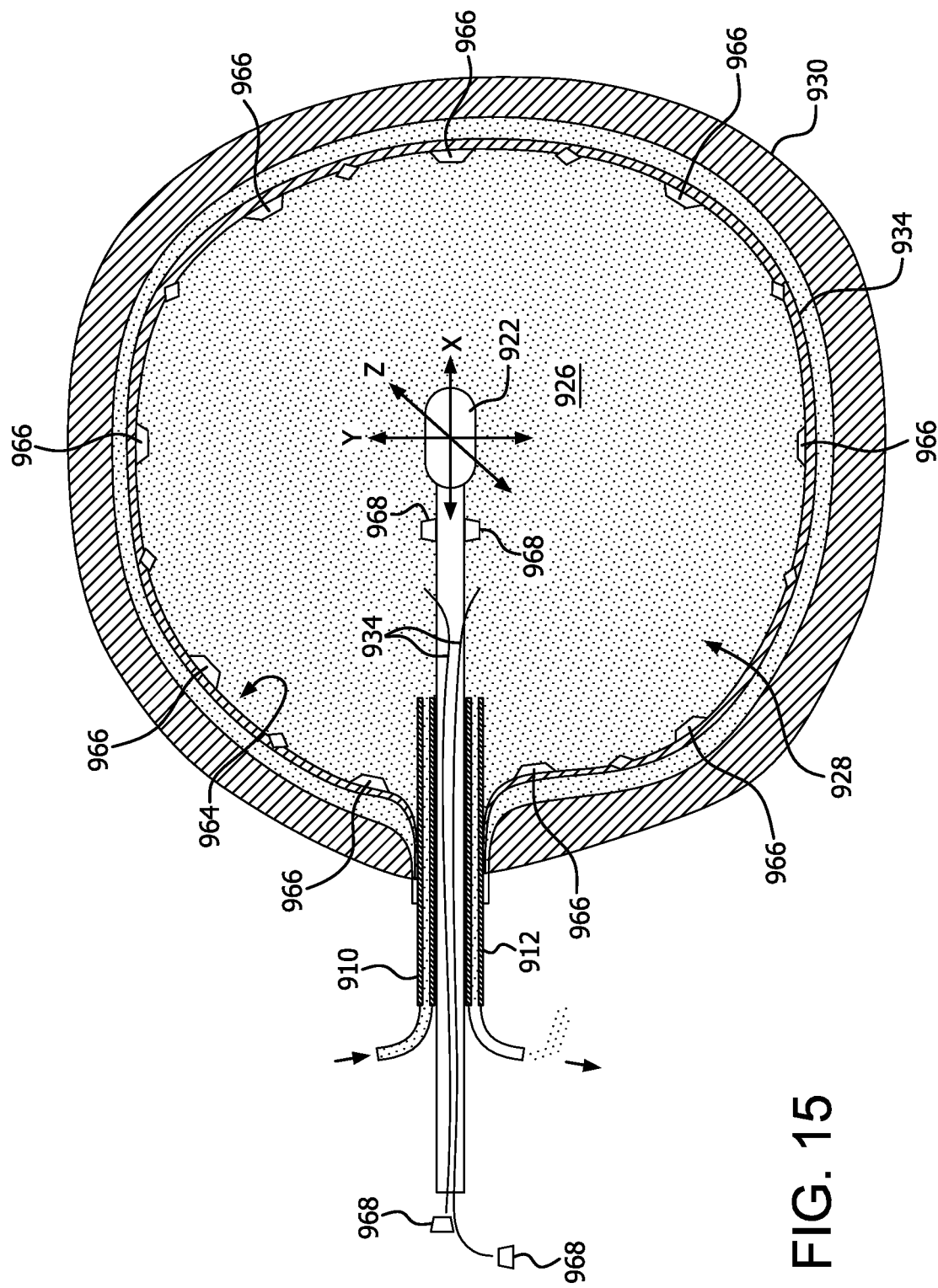
FIG. 15 is a drawing that is useful for understanding an alternative embodiment X-ray sensing element.

Referring now to FIG. 15, there is illustrated an alternative embodiment balloon applicator 964 which is similar to the balloon applicator described in relation to FIG. 10. In this embodiment, the XRSE 966 are comprised of simple passive elements that are responsive to X-ray energy such that each XRSE 966 will fluoresce or radiate photonic energy. In some scenarios, the intensity of the fluorescence will correspond to a level of X-ray energy impinging upon the XRSE. As the X-ray energy increases, the XRSE will fluoresce more intensely. Conversely, as the X-ray energy decreases, the XRSE will fluoresce less intensively. In some scenarios, the XRSE can be configured to undergo a color change in response to exposure to X-ray energy.

In some scenarios, the XRSE 966 described herein can operate in a manner that is similar to the operation of X-ray dosimeter badges used by persons who work with X-ray equipment. As is known, the material (aluminum oxide) used with some such X-ray dosimeter badges will give off visible light when exposed to X-ray radiation and then irradiated with a specific wavelength of laser light. The released energy of excitation can be measure to determine radiation dose. Accordingly, it is anticipated that in some scenarios, a laser exciter source can be provided within the balloon applicator to facilitate the X-ray dosimetry measurements described herein.

The response of the XRSE 966 can be captured in real-time by one or more imaging devices which are disposed within the interior of the balloon applicator. These imaging devices are advantageously arranged to capture in real-time the fluorescent response of the XRSE when they are excited by X-ray energy. In some scenarios, the one or more imaging devices can be electronic imaging devices 968. For example, the electronic imaging devices can comprise CMOS or CCD types of imaging sensors, which are well-known in the art. Digital data from these image sensors 968 can be communicated by wired or wireless communication means to the control system (e.g., to system controller 226). In an alternative scenario, the one or more electronic imaging devices can be disposed external of the balloon applicator. In such a scenario, images of an interior of the balloon applicator 964 can be acquired using one or more optical fibers 934. The optical fibers 934 couple optical image information from an interior of the balloon applicator to one or more electronic imaging devices 970 which are disposed external of the balloon applicator. In some scenarios, the electronic imaging devices 968, 970 can correspond to the IP camera/sensor 202 shown in FIG. 2, and can communicate imaging data to IP camera (base) 216.

The electronic imaging devices described herein can facilitate real-time video image capture showing the interior surface of the balloon, including real-time video imaging of the XRSE 966. Consequently, a treatment practitioner can receive a visual indication of X-ray dose applied to surfaces of the balloon interior based on a degree or intensity of the fluorescent response produced by XRSE when exposed to X-ray energy.

In some scenarios, an evaluation of the X-ray treatment can involve a visual observation of a sensor intensity or color change. In other scenarios, this visual evaluation can be based on an observation of a duration of time that fluorescence has occurred while observing the X-ray application. However, it can be advantageous to evaluate the real-time video imaging using system controller 226. This process can involve assigning to each of the XRSE a unique index number or address that can thereafter be monitored by the control system. The control processor 226 can then evaluate the degree of color change and/or fluorescence which occurs at each of the XRSE. This information can then be used to determine a time varying X-ray intensity detected at each of the XRSE over a duration of the X-ray treatment time. It can also be used to model an X-ray beam direction, shape, and intensity during a period of time associated with the X-ray treatment.

From the foregoing it will be understood that the sensor information captured by the XRSE 932, 966 can be useful to derive a real-time model of an X-ray beam and/or an X-ray dose applied to tissues surrounding the balloon applicator. The information thus gathered can then be compared to a predetermined treatment plan. The comparison described herein can involve an evaluation of how well the actual X-ray beam pattern matches the treatment plan. The comparison can also involve a determination of the exact dose of X-ray radiation applied to various tissue locations by the X-ray generating element. These results can be automatically compared to a radiation dose specified by a radiation treatment plan. In some scenarios, the results can be displayed to a treatment specialist on a computer display. Further, or in the alternative, the results of the monitoring can be automatically compared in real time to the amount of X-ray radiation to be applied by an X-ray source to the tumor bed in accordance with a radiation treatment plan.

In the event that actual X-ray treatment does not match a treatment plan, the X-ray treatment practitioner can be alerted. Further, a follow up radiation treatment plan can be identified by the system controller 226 and/or SBTPS 236. The follow up radiation treatment plan can be implemented immediately while the balloon applicator is still in place or at a later time.

Alternatively, if the actual dosages of X-ray radiation applied at a specified location are inconsistent with the radiation treatment plan, then adjustments can be made dynamically during a radiation treatment session. These adjustments can involve selectively modifying treatment operation to better conform to the treatment plan. Such adjustments or modifications can be performed by the control system automatically and/or under the control of a radiation treatment specialist. In some scenarios, these adjustments can involve terminating a treatment session prematurely if it poses a risk to the patient. But in other scenarios, the adjustments can include increasing the duration of a radiation treatment plan and/or dynamic modification of the sculpted X-ray beam to achieve a result that is more consistent with treatment plan.

Figure 16:
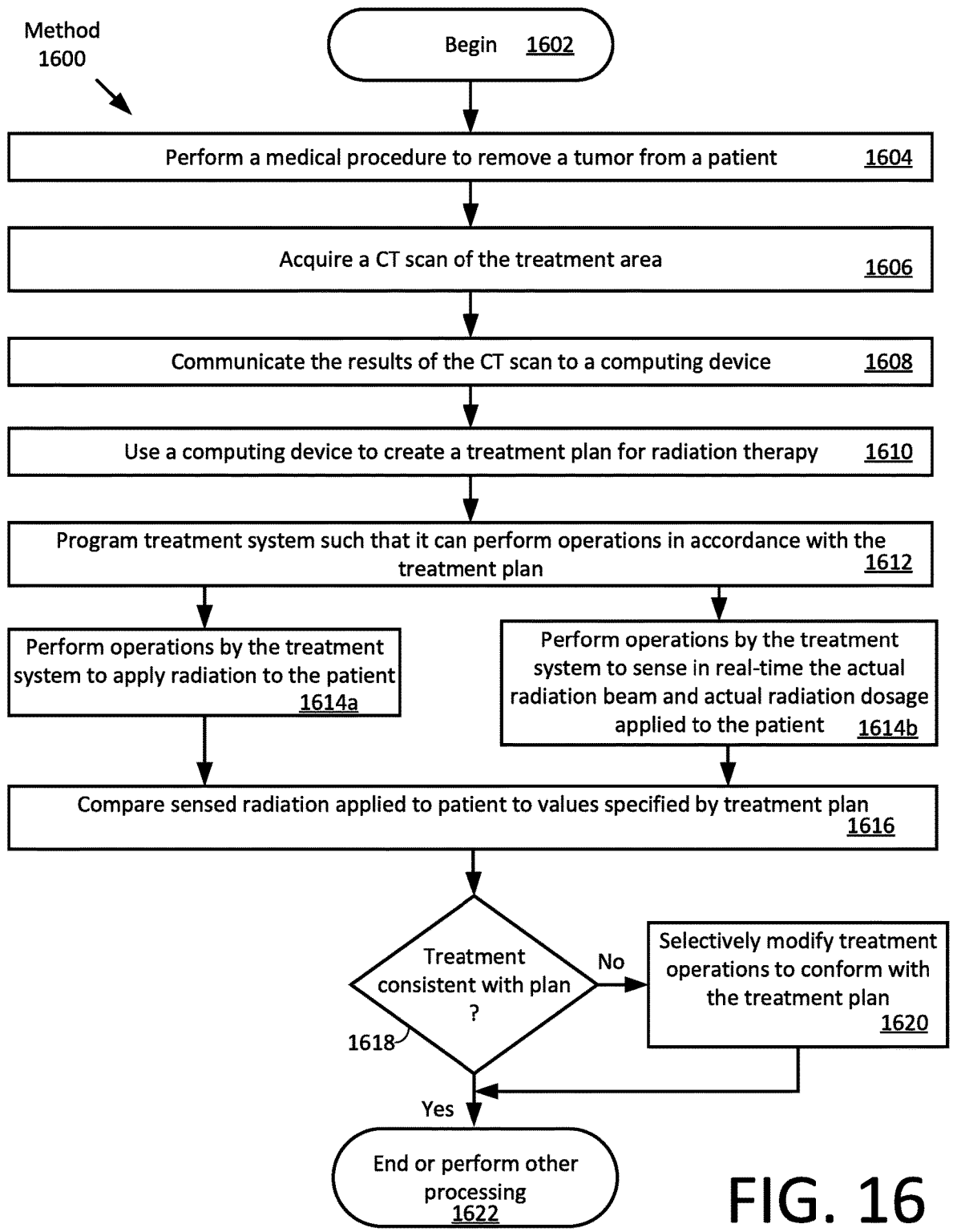
FIG. 16 is a flowchart which is useful for understanding how a robotic X-ray system can be used to facilitate Brachytherapy and/or intra-operative radiation therapy (IORT).
Figure 17:
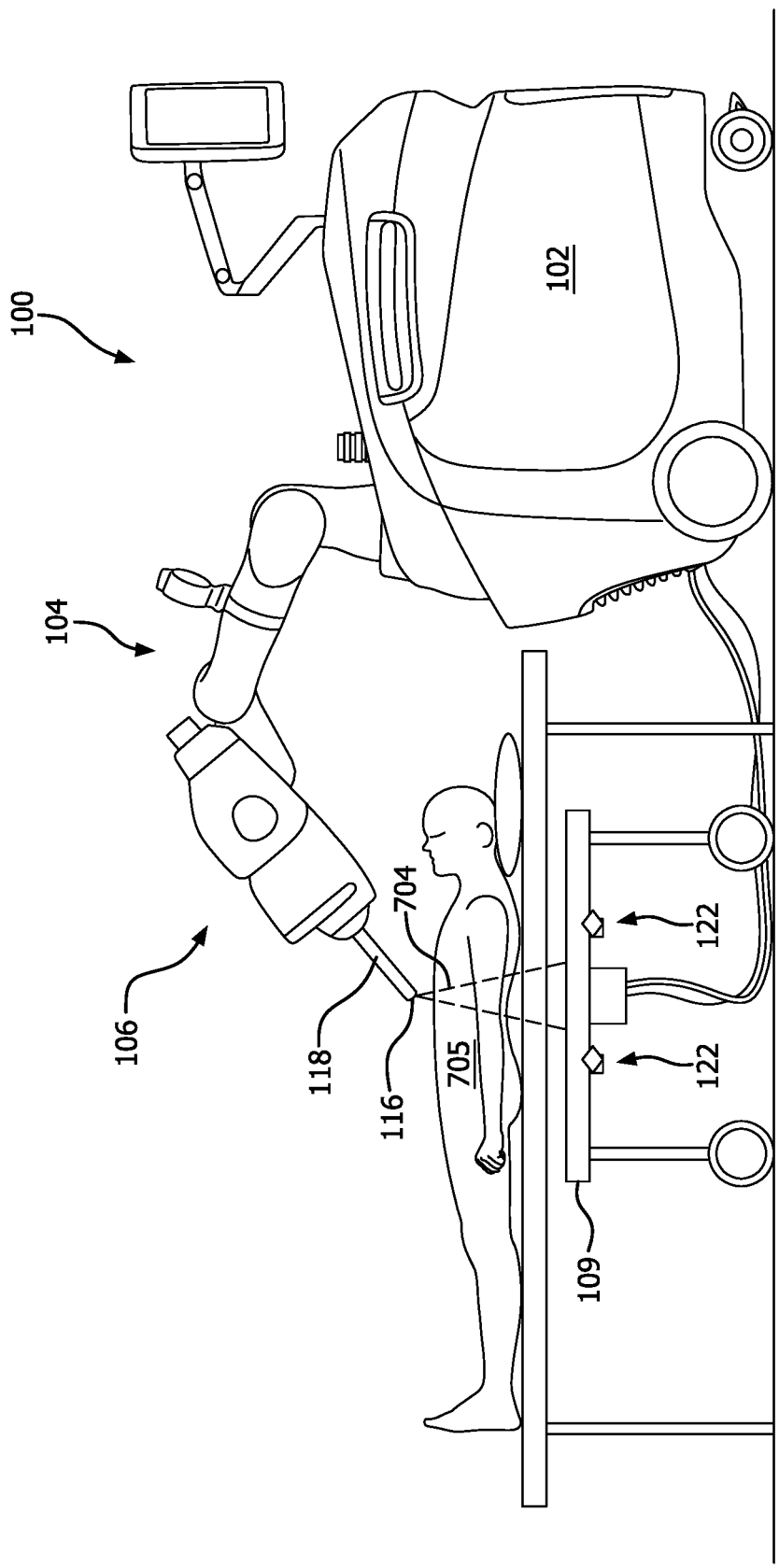
FIGS. 17-20 are a series of drawings that are useful for understanding a process whereby tomosynthesis is performed using a robotic X-ray system.
Figure 18:
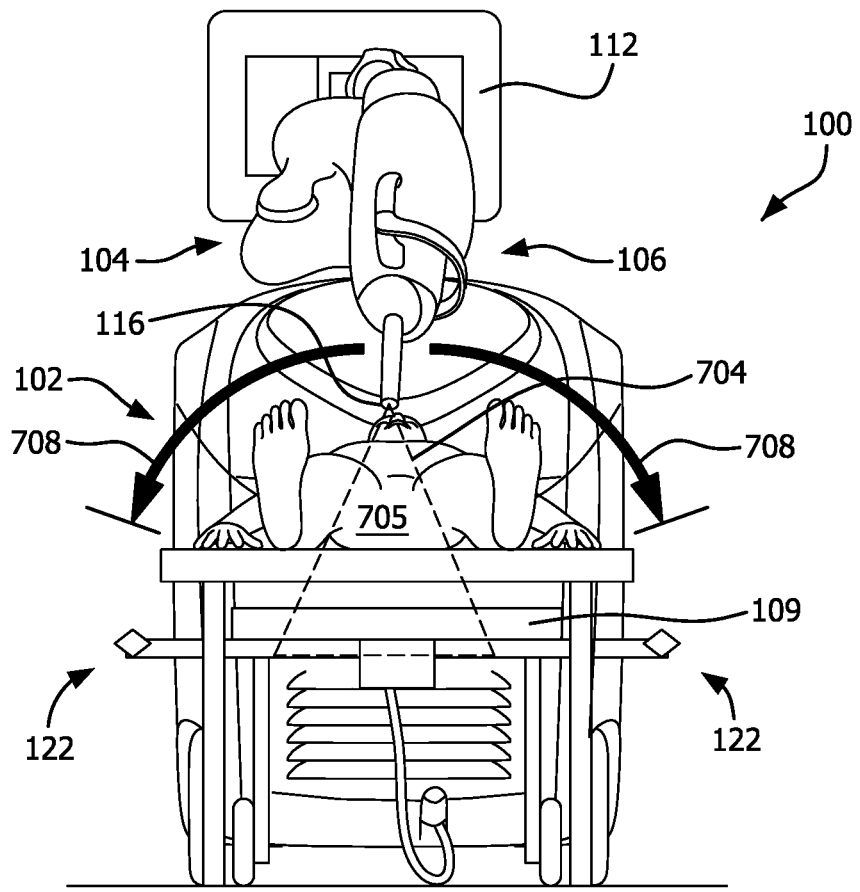
Figure 19:
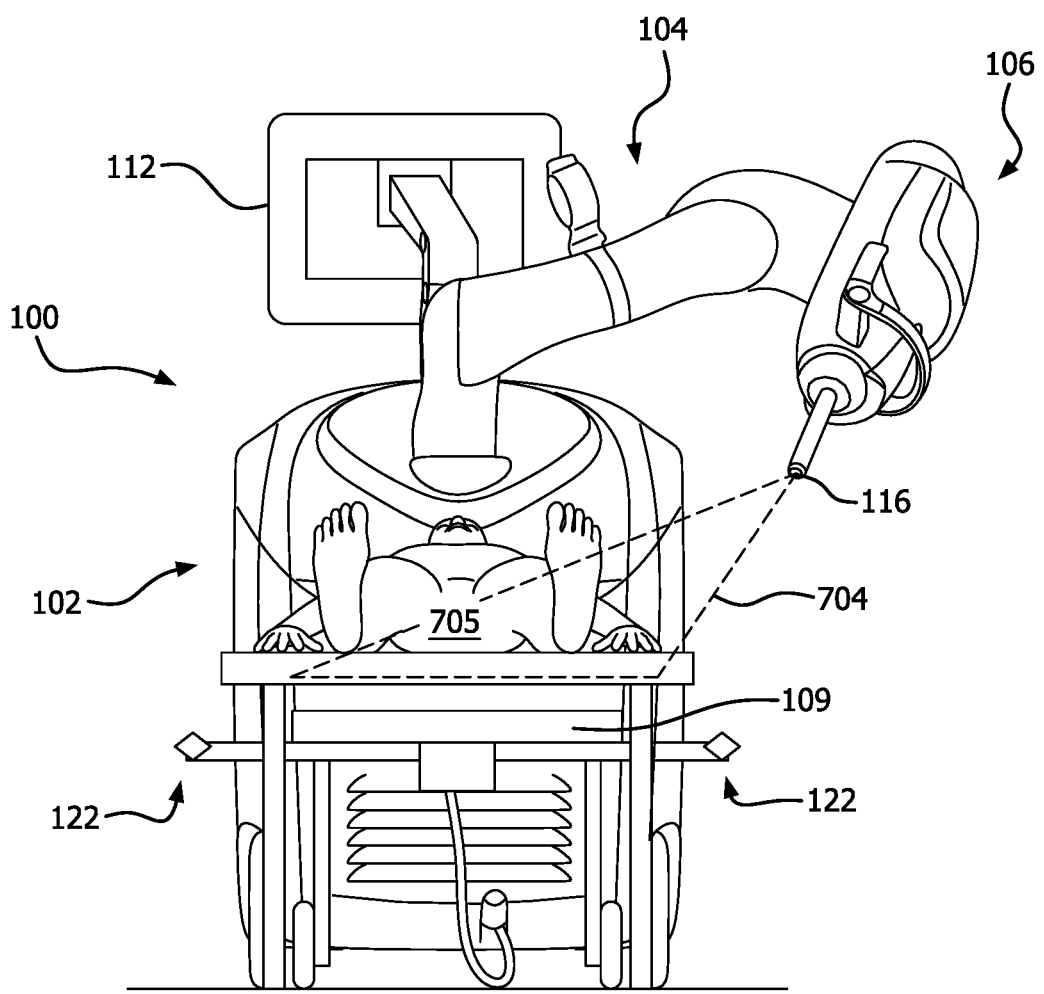
Figure 20:
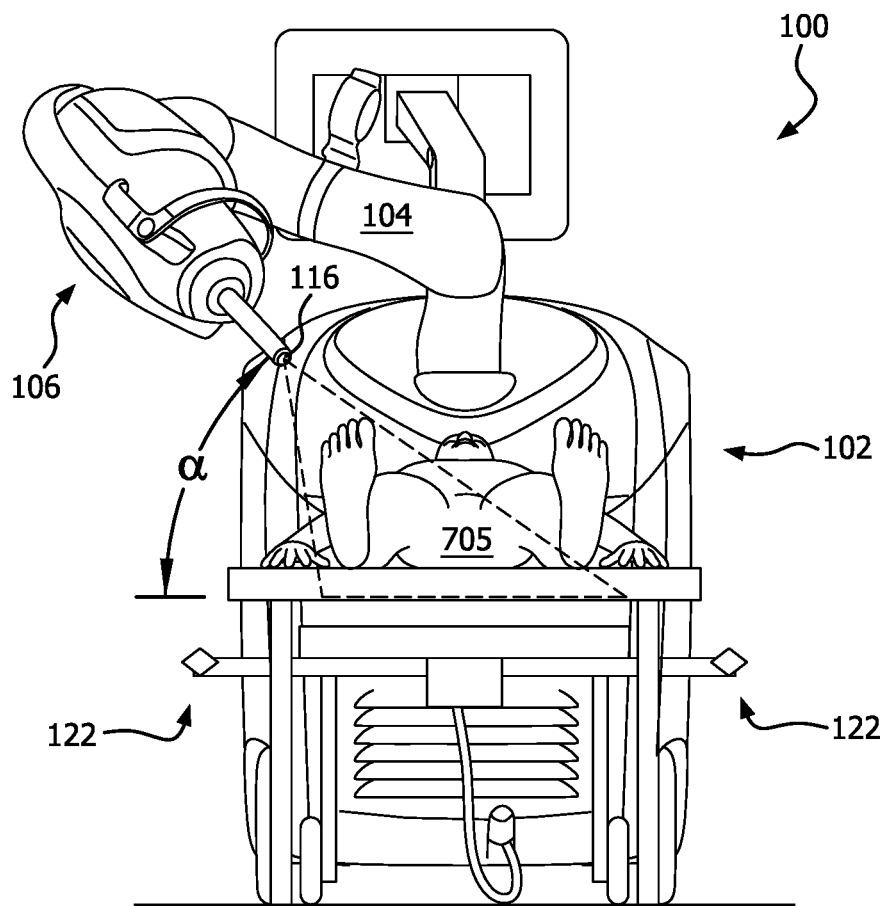

Referring now to FIG. 16, there is provided a flow diagram of an illustrative method 1600 for using a X-ray treatment system (e.g., Robotic Sculpted Beam X-ray System 100) to treat a patient with cancer. Method 1600 begins at 1602 and continues to 1604 where a medical procedure is performed to remove a tumor from a patient. Next at 1606, a scan of the treatment area is acquired. In some scenarios, this scan can be a CT scan. However, other types of medical scans which are now known or known in the future can also be used for this purpose. In some scenarios, the scan of the treatment area can be performed with the X-ray treatment source positioned in the wound cavity. Accordingly, the resulting CT scan will show the position and orientation of the X-ray treatment source within the patient. In some scenarios, the imaging scan can be facilitated by using the system 100 so that the same device used for X-ray treatment can also be used to facilitate the medical imaging needed to facilitate such treatment.

The results of the scan can be communicated at 1608 to a computing device (e.g., SBTPS 236 of FIG. 2). Thereafter at 1610, the computing device can be used to create a treatment plan for radiation therapy. For example, the treatment plan can be an IORT treatment plan whereby X-ray radiation is applied to a tumor bed from which the tumor has been removed. The treatment plan is created using a software application (e.g., software application 324) installed on the computing device or accessible via a virtualization platform provided by a server.

The X-ray treatment system (e.g., Robotic Sculpted Beam X-ray System 100) is programed in 1612 such that it can perform operations in accordance with the treatment plan. This programing can be achieved by: communicating the treatment plan from the computing device to a control system for the X-ray treatment system (e.g., system controller 226). Thereafter, operations by the control system are carried out to set operational parameters and other values in preparation for proceeding with the treatment plan.

Once the X-ray treatment system has been configured, X-ray radiation is applied by the system to the patient at 1614*a*. This application of X-ray radiation should occur in accordance with the treatment plan. Concurrently with the X-ray treatment the system at 1614*b* will sense in real-time the actual X-ray radiation beam intensity and/or radiation dosage applied to the patient. This sensing can facilitated by a balloon applicator with XRSE as described herein. At 1616 the system controller can compare the actual radiation dosages being delivered to tissue locations comprising the tumor bed with values specified by the radiation treatment plan. In some scenarios, this evaluation can involve a determination based on a derived X-ray beam model based on sensed data from the XRSE. If other scenarios, the comparison can be based on a total X-ray dose delivered to various locations defining the tumor bed. The dosage information can be based on the sensed data from the XRSE.

At 1618 a determination is made as to whether any aspect of the radiation treatment is at variance with the radiation treatment plan. This determination can be made during the treatment and/or after the treatment has been completed. If the treatment is consistent with the plan (1618: Yes), then the treatment operations can continue unimpeded until completed, and the process terminates at 1622. However, if actual treatment is determined to be at variance with the treatment plan (1618: No) then the system controller can modify treatment operations to better conform to the treatment plan. In some scenarios, these changes can occur automatically and dynamically during treatment to ensure better conformance and/or can occur under the control of a treatment specialist. The changes can involve modifications of X-ray beam shape, direction, intensity, and or duration of application to facilitate carrying out the treatment in accordance with the plan. Alternatively, the treatment information sensed by the XRSE can be used to prepare a follow up radiation treatment plan. Such a follow up treatment plan can be carried out to conclusion while the X-ray source remains disposed within the patient to facilitate final IORT operations.

From the foregoing it may be understood that the XRSE sense applied radiation from the radiation source. Based on this sensor data and information concerning the location/orientation of the X-ray source, the control system for the X-ray system can evaluate the X-ray operations. For example, the control system can compare at least one parameter of the applied radiation which has been sensed by the XRSE to a corresponding parameter of a predetermined radiation treatment plan. For example, some parameters of the applied radiation that can be evaluated for this purpose can include X-ray beam duration, beam intensity, and a three-dimensional radiation pattern associated with the applied radiation. Consequently, a determination can be made as to whether one or more requirements of a predetermined radiation treatment plan have been satisfied.

In some scenarios, the comparing operations performed by the control system as described herein may involves comparing sensed radiation intensity values detected in each of a plurality of different beam vector directions 504 extending from the radiation source. These sensed intensity values can be compared to corresponding radiation intensity values expected for the different beam vector directions as specified by a predetermined radiation treatment plan.

According to one aspect, measurement data from the XRSE can be used to generate estimated information about a three-dimensional radiation pattern produced by the radiation source for portions of the three-dimensional radiation pattern that are not directly sensed by the XRSE. In some scenarios, this estimated information can involve a computer generated model of the three-dimensional radiation pattern that is based on measured data from the XRSE. In other scenarios, the estimated information can comprise interpolated values or estimated values determined using other known mathematical techniques. In such scenarios, the estimated information can be used to facilitate comparisons with regard to one or more of the beam vector directions 504 for which actual measurement data from the plurality of XRSE is not available.

The real-time beam monitoring described herein advantageously facilitates operations involving dynamic control of the X-ray radiation source during a treatment session. These dynamic control operations can be performed in response to an analysis of the measurement data from the XRSE. In some scenarios, such dynamic control of the radiation source may involve selectively conforming a three-dimensional radiation pattern produced by the radiation source to a planned three-dimensional radiation pattern specified by a predetermined radiation treatment plan. In other scenarios, the dynamic control can involve selectively controlling a radiation dosage applied to the patient tissue. In particular, the radiation source can be controlled to conform an applied radiation dosage at a plurality of patient tissue locations to a planned radiation dosage specified by the radiation treatment plan for the plurality of patient tissue locations. For example, these various patient tissue locations can be aligned with a plurality of different beam vector directions relative to or originating from the radiation source.

In some scenarios, the applied radiation dosage at each of the various patient tissue locations can be selectively controlled during the treatment session by dynamically varying a three-dimensional radiation pattern produced by the radiation source during the treatment session. In other scenarios, the applied radiation dosage at each of the patient tissue locations can be dynamically controlled during the treatment session by selectively varying a duration of time that radiation is applied at each of the plurality of patient tissue locations. In such scenarios, the goal is to conform the actual radiation treatment to a predetermined treatment specified by a radiation treatment plan.

Tomosynthesis With a Multipurpose Robotic X-ray System

There are many different types of medical imaging techniques which can be used to facilitate the radiation treatment planning described herein. These imaging techniques use various different technologies and methods to achieve a desired imaging product. Among the most basic of these is conventional radiography or X-ray imaging, which uses ionizing radiation to generate images of the body. In conventional radiography, a single image is recorded for later evaluation. In a computed tomography (CT) systems (which is sometimes referred to as computed axial tomography or CAT), many X-ray images are recorded as a detector moves around the patient's body. A computer reconstructs all the individual images into cross-sectional images or "slices" of internal organs and tissues. With CT, a motorized table moves the patient through a circular opening in the CT imaging system while an X-ray source and a detector assembly within the system rotate around the patient. The X-ray source produces a narrow, fan-shaped beam of X-ray radiation that passes through a section of the patient's body and detectors opposite the X-ray register the X-rays that pass through the patient's body to form a scan. The scan is then used in a process of creating an image. Many different "scans" (at many angles through the patient) are collected during one complete rotation of the detector assembly. For each rotation of the X-ray source and detector assembly, the image data are sent to a computer to reconstruct all of the individual scans into one or multiple cross-sectional images (slices) of the internal organs and tissues. Reconstruction is performed using an inverse Radon transformation.

Digital Tomosynthesis ("DT") is an imaging technique that is somewhat similar to CT. With DT, ionizing radiation (e.g. X-ray radiation) is again used to obtain multiple two-dimensional (2D) projection images of a subject (e.g., a patient) from a plurality of different angles as an X-ray source moves over a predetermined path. From these projection images, a computer system reconstructs section or slice images of the subject. One distinction between CT and DT is that the range of angles that are used. For example, the total angular range of movement in the case of DT is often less than 40°. In this sense DT may be considered to be a form of limited angle tomography. In conventional DT systems, the image reconstruction is often obtained using a technique known as filtered back projection (FBP). As is known, FBP is a type of inverse Radon Transformation.

The X-ray system 100 has the potential to be used for multiple purposes, which can include tasks associated with both tomosynthetic imaging and therapeutic treatment. By controlling the position of one or more robotic arm joints, the robotic arm can control a position of the treatment head relative to the patient. The precise and highly adaptable robotic arm, when combined with special features of the X-ray source described herein allow such a system to be used for carrying out medical imaging. With an advanced control system, such imaging can be extended to include digital tomography or DT. Further, the highly adaptive nature of the robotic arm and the X-ray source in such an X-ray system can permit the same system to be used for carrying out therapeutic X-ray treatments, including but not limited to IORT and Brachytherapy.

Referring once again to FIG. 1, An X-ray system 100 can comprise a solid-state X-ray imaging array 109. In some scenarios, the imaging array 109 can be separate with respect to the base unit 102 as shown in FIG. 1. However, in other scenarios, the imaging array 109 can be an integral component of the base unit 102 which is extendable from the base unit 102 (e.g., on wheels and/or with a mechanical arm). The imaging array 109 is communicatively coupled to the X-ray system by means of a wired or wireless communication link. The purpose of the imaging array will be discussed below in greater detail.

The various components comprising the X-ray generating system in system 100 can be controlled so that they are selectively optimized for a therapeutic radiation treatment and/or certain patient imaging operations as hereinafter described. The therapeutic radiation treatment can in some scenarios include IORT interaction with tumor bed tissue, whereby the radiation will have minimal effects at deeper tissue depths. For example, a superficial radiation therapy (SRT) type of X-ray source can be used for this purpose. As will be appreciated, an SRT type of X-ray unit produces low energy X-rays that is suitable for this purpose. In other scenarios, a therapeutic treatment can involve Brachytherapy.

In some scenarios, the solid-state X-ray imaging array 109 can be used to capture two-dimensional (2D) X-ray projection images of a subject patient when the patient is exposed to X-rays produced by the X-ray source. These 2D X-ray projection images can be obtained by positioning the X-ray source at a plurality of different locations relative to the patient. In such a scenario, the 2D X-ray projections images will be captured with the X-ray source positioned at a plurality of different angles (relative to the patient) as the X-ray radiation source (e.g., the X-ray tube) is moved by the robotic arm 104 over a predetermined path. Solid-state X-ray imaging arrays are well-known in the art and therefore will not be described here in detail. However, it should be understood that captured 2D X-ray projection images can be communicated to an on-board processing element (such as system controller 226), a separate image processing computer (e.g., workstations 234 and/or RTP workstation 236) and/or a data storage device 240 for later processing.

As hereinafter described in greater detail, the X-ray system in FIGS. 1-6 can comprise a multifunctional X-ray system which can be adapted or configured for a plurality of different tasks in a medical facility. One such task can involve medical imaging, and more particularly digital tomography or DT. Referring now to FIGS. 17-21 the robotic arm 104 can precisely control a position of an X-ray treatment head 116 which serves as an X-ray radiation source. In the scenario shown in FIG. 17, the X-ray treatment head 116 is shown positioned relative to a subject patient 705 such that a beam 704 of X-ray radiation can be projected through a portion of the patient which is to be imaged. The X-ray imaging array 109 is disposed on a side of the patient opposing the X-ray treatment head such that it positioned to capture two-dimensional (2D) X-ray projection images of the subject patient 705 when the patient is exposed to X-rays produced by treatment head 116.

Figure 21:
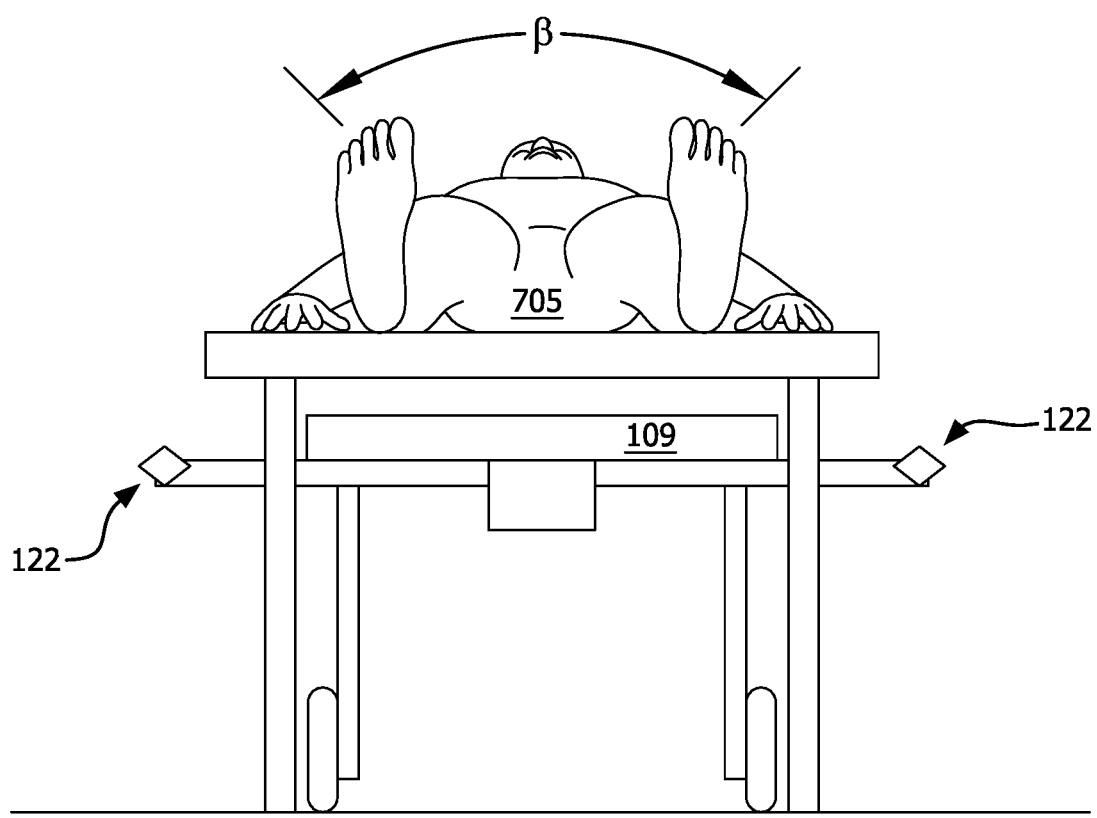
FIG. 21 is a drawing which is useful for understanding a range of scan angles which can be used by a robotic X-ray system when performing tomosynthesis operations.

The 2D X-ray projection images are captured or obtained at times when the X-ray treatment head 116 is located at a plurality of different locations relative to the patient. This concept is illustrated in with reference to FIGS. 18-21 which show that the X-ray treatment 116 head is moved by the robotic arm 104 along a predetermined path 708 in a peripheral space around the patient. The X-ray treatment head 116 is moved along the predetermined path 708 by selectively controlling (e.g., with system controller 226) a plurality of joint positions associated with a plurality robot arm joints 120. As shown in FIG. 21, the predetermined path 708 can in some scenarios define an arc which has a central angle β of between 15° and 40°.

In the system described herein, the X-ray beam 704 can be shaped or sculpted to primarily direct X-ray radiation toward the X-ray imaging array 109. For example, the beam can be controlled in a manner similar to that shown in FIG. 6 to create a cone geometry in which X-ray radiation is primarily directed toward the patient and the X-ray imaging array 109.

Referring now to FIGS. 22A and 22B, it can be observed that a cap 710 can be disposed on the treatment head 116. The cap can be provided when the X-ray system 100 is used for DT operations so as to facilitate beam shaping an beam hardening. The cap 710 can include a shielded portion 714 which extends circumferentially around the treatment head 116 so as to ensure that the transmission of X-ray radiation does not occur in undesired directions. An X-ray window 712 allows collimation of X-ray radiation so that the energy is transmitted in a limited range of angles. This collimation can be configured to facilitate a cone beam geometry in which X-ray radiation is primarily directed to the patient and the X-ray imaging array 109. The X-ray window 712 can be formed of a suitable material such as aluminum so as to facilitate beam filtering and hardening. The cap 710 can include a registration notch or groove which engages a corresponding structure on the treatment head so that the cap can only reside on the treatment head in one position. Consequently, the X-ray window 712 can be known in advance, and may be registered with a shaped X-ray beam that is produced at the treatment head.

For purposes of carrying out DT operations as described herein, the X-ray system 100 can be selectively controlled to facilitate an X-ray beam having a suitable intensity. This can involve selectively applying an appropriate accelerating voltage within the X-ray source for purposes of forming the X-ray beam. For example, the system controller can apply an energy level of 120 kV for this purpose, which is common for use in DT. The system controller 226 can control the energy associated with the electron beam by selectively varying the output voltage of the HV power supply 228.

A laser field of view (FOV) projector 204 can be disposed on the cap 810. The laser FOV projector can be configured to project a pattern of visible laser light 716 on the patient 705. When projected on the patient, the locations of this pattern of laser light 716 will correspond to locations which will be exposed to an X-ray beam that is produced by the X-ray system during DT operations. Accordingly, a technician can visibly verify that certain desired portions of the patient anatomy will be illuminated with X-ray radiation during the DT procedure.

The robotic arm 104 can control a position of the X-ray treatment head 116 so that the beam is always oriented in a direction toward the X-ray imaging array 109. In some scenarios, a primary direction of the beam 704 can be dynamically controlled concurrent with the movement of the X-ray treatment head 116. For example, the direction of the beam can be varied as the X-ray treatment head is moved by the robotic arm along the predetermined path. The direction of the X-ray beam can be controlled by selectively varying the position and/or orientation of the treatment head, using the robotic arm. The direction of the X-ray beam can also be modified by using the beam shaping methods described herein with respect to FIGS. 5 and 6.

With the arrangement as described, the 2D projection images are captured by the X-ray imaging array 109 at different times when the X-ray treatment head 116 is located at a plurality of different locations along the predetermined path 708. Consequently, the 2D X-ray projections images will be captured with the X-ray source disposed at a plurality of different angles α (relative to the patient) as the X-ray radiation source (e.g., the X-ray tube) is moved by the robotic arm 104 over a predetermined path 708.

Solid-state X-ray imaging arrays are well-known in the art and therefore will not be described here in detail. However, it should be understood that captured 2D X-ray projection images from the X-ray imaging array 109 can be communicated to an on-board processing element (such as system controller 226). These communications can be facilitated by a wired or a wireless link which communicatively couples data from the X-ray imaging array 109 to the X-ray system 100. In other scenarios, these projection images can be communicated to a separate image processing computer (not shown) and/or a data storage device provided in the X-ray system 100.

Concurrent with obtaining each 2D projection image, the system controller 226 will determine a corresponding location of the X-ray radiation source as it is moved along the predetermined path by the robotic arm. For example, this information can be determined based on information received by the system controller 226 (directly or indirectly) from a plurality of joint position sensors 115 which are associated with the joints 120 comprising the robotic arm 104. In some scenarios, this position information can be used by the system controller 226 to determine a specific angle α and an exact location of the X-ray radiation source relative to the X-ray imaging array.

Once all of the 2D projection images have been obtained in this manner, the multiple 2D projection images and the location information can be processed in a computer processing element (e.g. SBTPS 236) to perform a digital tomosynthesis ("DT") operation. As part of this DT operation, section or slice images of the subject patient are reconstructed based on the 2D projection images. This reconstruction can take place in a manner that is similar to that which is used in a conventional DT systems. For example, in some scenarios the image reconstruction can be performed using a conventional technique known as filtered back projection (FBP). As is known, FBP is a type of inverse Radon Transformation.

In order to facilitate the X-ray imaging described herein, it is advantageous for the system 100 to be able to determine a location of the X-ray imaging array 109 relative to the source of X-ray radiation (which in this case is the treatment head 116). This information can be useful for determining an appropriate path 708 of the treatment head 116. The information also facilitates the FBP processing associated with the reconstruction of slice images of the subject. In this regard, fiducial markers 122 can facilitate position sensing of the X-ray imaging array 109. The fiducial markers 122 also facilitate registration of images acquired by the imaging array. The exact type of fiducial markers selected for this purpose will depend on the registration system utilized. However, in some scenarios, the fiducial markers can be simple optical markers suitable for detection for an imaging device.

The one or more fiducial markers 122 are advantageously fixed to the X-ray imaging array 109 in location(s) that allows them to be imaged by an IP camera/imaging sensor 202. The optically imaged positions of these fiducial markers 122 can facilitate the determination of the appropriate path 708, and the position of the X-ray imaging array 109 relative to the treatment head 116. The position information can then be used to facilitate the image collection process, and the image reconstruction process.

Therapeutic Treatment Operations

The X-ray system 100 is multifunctional insofar as it can be used to perform therapeutic treatment such as IORT, Brachytherapy, and External Beam Radio Therapy (EBRT) when it is not being used for tomographic imaging as described herein. For example, consider an IORT scenario in which a surgical procedure has been performed to remove a cancerous tumor from a patient. During the surgical procedure, a practitioner may use the X-ray system to perform certain medical imaging operations as described herein. The surgeon can review the reconstructed images based on the 2D projection images and then initiate an IORT procedure using the X-ray system 100. This IORT procedure is illustrated in FIG. 7 which shows the surgeon can use the robotic arm 104 to reposition the X-ray treatment head 116 with respect to the subject patient 705. In particular, the X-ray source can be repositioned within a tumor bed of the removed cancerous tumor. Thereafter, the X-ray source can be activated while the treatment head 116 is disposed at the treatment location so as to carry out a therapeutic X-ray treatment of the subject patient. In some scenarios, the DT imaging described herein can be performed during the procedure, after the tumor has been removed. Such intraoperative imaging can be particularly useful to help with radiation therapy planning (RTP) because it allows the practitioner to image the tissue to be irradiated immediately after tumor removal, and just before the IORT procedure is initiated.

The usefulness of the DT imaging described herein can be further enhanced by using an image fusion technique. In such a scenario, pre-operative volumetric imaging of a patient undergoing treatment (e.g. tumor removal) can be performed using a conventional imaging method. Examples of suitable volumetric imaging methodologies which can be used for this purpose can include computed tomography (CT) and magnetic resonance imaging (MRI). However, the solution is not limited in this regard and any other suitable volumetric imaging technology can also be used for this purpose, whether now known, or known in the future. The acquired pre-operative volumetric imaging can then be stored in a database, such as patient data storage device 240. Thereafter, a surgical procedure can be performed on the patient, such as removal of a cancerous tumor. This step can be followed by the intraoperative DT imaging described herein. But rather than simply rely upon the intraoperative DT imaging for purposes of the RTP, an improved or enhanced result can be obtained in a deformable image fusing step. This step can involve fusing the higher quality pre-operative volumetric imaging with the somewhat lower quality intraoperative results obtained using DT. Deformable image fusing algorithms and methods are well known in the art and therefore will not be described here in detail. However, it will be appreciated that any such deformable fusion algorithm, whether now known or known in the future, can be used to facilitate the fusing process described herein.

It will be understood that the internal anatomy of the patient undergoing treatment will necessarily be changed somewhat as a result of the surgical procedure involving cancerous tumor removal. The deformable image fusing step described herein will therefore make use of anatomical landmarks to facilitate image registration, but will advantageously fit the pre-operative volumetric imaging with the intraoperative DT imaging. The resulting fused volumetric image will combine the higher quality pre-operative volumetric imaging, with the lesser quality but more current results obtained using the intraoperative DT imaging. Deep learning techniques can be used to develop and guide this deformable image fusion process. Further, artificial intelligence can be applied to the fusion process to ensure that the deformable image fusion process. Once the deformable fusion process is complete, the RTP process can continue so as to facilitate any IORT treatment. Such fused image can be particularly useful to help with RTP because it allows the practitioner to image the tissue to be irradiated immediately after tumor removal, and just before the IORT procedure is initiated.

Notably, a X-ray beam 704 that is suitable for tomosynthesis as described herein may not be suitable for carrying out a therapeutic treatment, such as IORT. However, a beam shaping capability of the X-ray source can be used to dynamically change the beam shape so that it is suitable for the particular therapeutic treatment. Accordingly, system controller 226 can be used to selectively control the X-ray source to generate an X-ray beam 704 having a first beam shape for purposes of obtaining the 2D projection images, and subsequently generate an X-ray beam having a different shape for purposes of carrying out the therapeutic X-ray treatment. Similarly, the control system can control an X-ray beam intensity. In this regard it should be understood that the beam intensity used for imaging may be controlled by the control system so that it is different as compared to the beam intensity used for therapeutic purposes (e.g. during and IORT procedure). The X-ray system 100 can be controlled to emit low energy X-ray radiation levels for IORT. For example, in some scenarios the X-ray system 100 can reduce X-ray energy to about 50 kV or less for this purpose.

Although the systems and methods have been illustrated and described with respect to one or more implementations, equivalent alterations and modifications will occur to others skilled in the art upon the reading and understanding of this specification and the annexed drawings. In addition, while a particular feature may have been disclosed with respect to only one of several implementations, such feature may be combined with one or more other features of the other implementations as may be desired and advantageous for any given or particular application. Thus, the breadth and scope of the disclosure herein should not be limited by any of the above descriptions. Rather, the scope of the invention should be defined in accordance with the following claims and their equivalents.

We claim:

1. A method for validation of a therapeutic X-ray treatment, comprising:
    using a robotic arm to control a position of a radiation source relative to patient tissue of a subject patient;
    facilitating a digital tomosynthesis ("DT") operation by using an X-ray imaging array to selectively capture a plurality of two-dimensional (2D) X-ray projection images as the radiation source produces X-rays and is moved by the robotic arm to a plurality of different locations relative to the subject patient over a predetermined path;
    using the results of the DT operation to facilitate development of a predetermined radiation treatment plan;
    using an applicator balloon surrounding the radiation source to control a distance between the radiation source and the patient tissue comprising a radiation treatment site;
    using a plurality of X-ray sensor elements (XRSE) supported on the applicator balloon at a plurality of distributed locations to sense applied radiation from the radiation source during the therapeutic X-ray treatment of the patient tissue;
    comparing at least one parameter of the applied radiation which has been sensed by the XRSE to a corresponding parameter of the predetermined radiation treatment plan; and
    based on the comparing, determining if one or more requirements of the predetermined radiation treatment plan have been satisfied.

2. The method according to claim 1, wherein the at least one parameter is selected from the group consisting of a duration of the applied radiation, an intensity of the applied radiation, and a three-dimensional radiation pattern associated with the applied radiation.

3. The method according to claim 1, wherein the comparing involves comparing a plurality of sensed radiation intensity values detected in each of a plurality of different beam vector directions extending from the radiation source, to a plurality of corresponding expected radiation intensity values for the plurality of different beam vector directions as specified by a planned three-dimensional radiation pattern.

4. The method according to claim 3, wherein the planned three-dimensional radiation pattern is specified by the predetermined radiation treatment plan.

5. The method according to claim 3, further comprising using measurement data generated by the XRSE to generate estimated information about a three-dimensional radiation pattern produced by the radiation source for portions of the three-dimensional radiation pattern that are not directly sensed by the XRSE.

6. The method according to claim 5, further comprising using the estimated information to facilitate the comparing with regard to one or more of the plurality of different beam vector directions for which actual measurement data from the plurality of XRSE is not available.

7. The method according to claim 1, further comprising using one or more fiducial markers to facilitate a determination of an orientation and a location of the radiation source relative to the patient tissue.

8. The method according to claim 1, further comprising dynamically controlling the radiation source during a treatment session responsive to measurement data from the XRSE.

9. The method according to claim 8, wherein the dynamic controlling of the radiation source involves selectively conforming a three-dimensional radiation pattern produced by the radiation source to a planned three-dimensional radiation pattern specified by the predetermined radiation treatment plan.

10. The method according to claim 1, further comprising dynamically controlling the radiation source during a treatment session responsive to measurement data from the XRSE to selectively control a radiation dosage applied to the patient tissue.

11. The method according to claim 10, wherein the radiation source is controlled to conform an applied radiation dosage at a plurality of patient tissue locations to a planned radiation dosage specified by the predetermined radiation treatment plan for the plurality of patient tissue locations.

12. The method according to claim 11, wherein the plurality of patient tissue locations are aligned with a plurality of different beam vector directions originating from the radiation source.

13. The method according to claim 11, wherein the applied radiation dosage at each of the plurality of patient tissue locations is selectively controlled during the treatment session by dynamically varying a three-dimensional radiation pattern produced by the radiation source during the treatment session.

14. The method according to claim 11, wherein the applied radiation dosage at each of the plurality of patient tissue locations is dynamically controlled during the treatment session by selectively varying a duration of time that radiation is applied at each of the plurality of patient tissue locations.

15. The method of claim 1, further comprising a deformable image fusing operation in which a pre-operative volumetric imaging of the subject patient is deformably fused with a plurality of image sections or slices obtained from the DT operation.

16. The method according to claim 1, further comprising concurrent with obtaining each 2D projection image, determining a location of the radiation source relative to the X-ray imaging array.

17. The method according to claim 1, wherein the predetermined path defines an arc which has a central angle of between 15° and 40°.

18. The method according to claim 1, further comprising:
using the robotic arm to position the radiation source with respect to the patient tissue so that the radiation source is disposed at a treatment location; and
activating the radiation source while it is at the treatment location to carry out the therapeutic X-ray treatment of the patient tissue.

19. The method according to claim 18, wherein the therapeutic X-ray treatment is an intra-operative radiotherapy treatment.

20. The method according to claim 1, further comprising selectively controlling the radiation source to produce a first X-ray beam pattern for purposes of obtaining the 2D projection images, and a second X-ray beam pattern for purposes of the therapeutic treatment.

21. A method for validation of a therapeutic radiation treatment, comprising:
facilitating a digital tomosynthesis ("DT") operation by using an X-ray imaging array to selectively capture a plurality of two-dimensional (2D) X-ray projection images as a radiation source produces X-rays and is moved by a robotic arm to a plurality of different locations relative to a subject patient over a predetermined path;
using the results of the DT operation to facilitate development of a radiation treatment plan;
using the robotic arm and an applicator balloon surrounding the radiation source to control a distance between the radiation source and patient tissue of the subject patient comprising a radiation treatment site;
sensing applied X-ray radiation from the radiation source during the therapeutic radiation treatment of the subject patient;
comparing at least one parameter of the applied X-ray radiation to a corresponding parameter of the radiation treatment plan; and
based on the comparing, determining if one or more requirements of the radiation treatment plan have been satisfied.

22. The method of claim 21, further comprising a deformable image fusing operation in which a pre-operative volumetric imaging of the subject patient is deformably fused with a plurality of image sections or slices obtained from the DT operation.

23. The method according to claim 21, further comprising concurrent with obtaining each 2D X-ray projection image, determining a location of the radiation source relative to the X-ray imaging array.

24. The method according to claim 21, wherein the predetermined path defines an arc which has a central angle of between 15° and 40°.

25. The method according to claim 21, further comprising:
using the robotic arm to position the radiation source with respect to the patient tissue so that the radiation source is disposed at a treatment location; and
activating the radiation source while it is at the treatment location to carry out the therapeutic radiation treatment.

26. The method according to claim 25, wherein the therapeutic radiation treatment is an intra-operative radiotherapy treatment.

27. The method according to claim 21, further comprising selectively controlling the radiation source to produce a first X-ray beam pattern for purposes of obtaining the 2D projection images, and a second X-ray beam pattern for purposes of the therapeutic radiation treatment, the second X-ray beam pattern being different as compared to the first X-ray beam pattern.

* * * * *